(12) United States Patent
Kenmoku et al.

(10) Patent No.: US 7,056,708 B2
(45) Date of Patent: Jun. 6, 2006

(54) METHOD OF PRODUCING POLYHYDROXYALKANOATE FROM ALKANE HAVING RESIDUE CONTAINING AROMATIC RING IN ITS MOLECULE

(75) Inventors: Takashi Kenmoku, Kanagawa (JP); Etsuko Sugawa, Kanagawa (JP); Tetsuya Yano, Kanagawa (JP); Takeshi Imamura, Kanagawa (JP); Tsutomu Honma, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 275 days.

(21) Appl. No.: 10/410,349

(22) Filed: Apr. 10, 2003

(65) Prior Publication Data
US 2003/0207412 A1 Nov. 6, 2003

(30) Foreign Application Priority Data
Apr. 26, 2002 (JP) ............................. 2002-126158

(51) Int. Cl.
C12P 11/00 (2006.01)
C12P 7/62 (2006.01)

(52) U.S. Cl. ...................................... 435/130; 435/135

(58) Field of Classification Search ................ 435/130, 435/135
See application file for complete search history.

(56) References Cited

U.S. PATENT DOCUMENTS

| | | | |
|---|---|---|---|
| 4,393,167 A | 7/1983 | Holmes et al. ................ 525/64 |
| 4,477,654 A | 10/1984 | Holmes et al. ............. 528/361 |
| 4,876,331 A | 10/1989 | Doi ............................. 528/361 |
| 5,135,859 A | 8/1992 | Witholt et al. .............. 435/135 |
| 5,191,016 A | 3/1993 | Yalpani ..................... 525/54.2 |
| 5,200,332 A | 4/1993 | Yamane et al. ............. 435/135 |
| 5,292,860 A | 3/1994 | Shiotani et al. ............ 528/361 |
| 5,334,698 A | 8/1994 | Witholt et al. .............. 528/354 |
| 5,811,272 A | 9/1998 | Snell et al. ................. 435/135 |
| 6,156,852 A | 12/2000 | Asrar et al. ................. 525/450 |
| 6,492,147 B1 | 12/2002 | Imamura et al. ........... 435/135 |
| 6,521,429 B1 | 2/2003 | Honma et al. .............. 435/135 |
| 6,586,562 B1 | 7/2003 | Honma et al. .............. 528/361 |
| 6,635,782 B1 | 10/2003 | Honma et al. ................ 560/53 |
| 6,645,743 B1 | 11/2003 | Honma et al. .............. 435/146 |
| 6,649,380 B1 | 11/2003 | Yano et al. .................. 435/135 |
| 6,649,381 B1 | 11/2003 | Honma et al. .............. 435/135 |
| 6,777,153 B1 * | 8/2004 | Yano et al. .................. 430/127 |
| 6,911,521 B1 * | 6/2005 | Kenmoku et al. .......... 528/295 |
| 2001/0029039 A1 | 10/2001 | Honma et al. .............. 435/135 |
| 2002/0052444 A1 | 5/2002 | Imamura et al. ............ 525/107 |
| 2002/0160467 A1 | 10/2002 | Honma et al. .............. 435/135 |
| 2003/0013841 A1 | 1/2003 | Imamura et al. ............ 528/271 |
| 2003/0096182 A1 | 5/2003 | Yano et al. ............. 430/108.5 |
| 2003/0096384 A1 | 5/2003 | Kenmoku et al. .......... 435/135 |
| 2003/0104300 A1 | 6/2003 | Kenmoku et al. ..... 430/108.22 |
| 2003/0113368 A1 | 6/2003 | Nomoto et al. ............. 424/450 |
| 2003/0194789 A1 | 10/2003 | Honma et al. .............. 435/135 |
| 2004/0067576 A1 | 4/2004 | Honma et al. ......... 435/252.34 |

FOREIGN PATENT DOCUMENTS

| | | |
|---|---|---|
| CN | 1321695 A | 11/2001 |
| EP | 0 416 624 A2 | 3/1991 |
| EP | 1 113 033 A2 | 7/2001 |
| EP | 1 130 042 A2 | 9/2001 |
| EP | 1 130 043 A2 | 9/2001 |
| EP | 1 188 782 A2 | 3/2002 |
| EP | 1 236 752 A2 | 9/2002 |
| EP | 1 236 754 A2 | 9/2002 |
| EP | 1 236 755 A2 | 9/2002 |
| EP | 1 245 605 A2 | 10/2002 |
| EP | 1 253 161 A2 | 10/2002 |
| EP | 1 253 162 A2 | 10/2002 |
| EP | 1 262 508 A2 | 12/2002 |
| EP | 1 275 727 A2 | 1/2003 |

(Continued)

OTHER PUBLICATIONS

Y.B. Kim et al., "Preparation and Characterization of Poly(β-hydroxyalkanoates) Obtained from *Pseudomonas oleovorans* Grown with Mixtures of 5-Phenylvaleric Acid and *n*-Alkanoic Acids," 24 *Macromol.* 5256-5260 (1991).

(Continued)

*Primary Examiner*—Herbert J. Lilling
(74) *Attorney, Agent, or Firm*—Fitzpatrick, Cella, Harper & Scinto

(57) ABSTRACT

The present invention provides a method of effectively producing polyhydroxyalkanoate having an aromatic substituted residue in its monomer unit. In the method of producing polyhydroxyalkanoate by using microorganisms, microorganisms capable of producing polyhydroxyalkanoate are cultured in a culture medium containing at least one starting compound selected from the group consisting of substituted alkanes represented by formula (1) to produce polyhydroxyalkanoate having, in its molecule, at least one unit selected from the group consisting of 3-hydroxy-substituted alkanoate units represented by formula (2):

$$R-(CH_2)_n-CH_2-CH_2-CH_3 \quad (1)$$

wherein R represents a residue containing a substituted aromatic ring, and n represents any integer of 1 to 8;

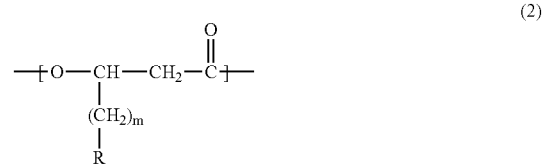

(2)

wherein R represents a residue containing a substituted aromatic ring, and n represents any integer of 1 to 8. In formulas (1) and (2), a residue R is as described in the specification.

20 Claims, 1 Drawing Sheet

FOREIGN PATENT DOCUMENTS

| | | |
|---|---|---|
| JP | 59-190945 | 10/1984 |
| JP | 63-226291 | 9/1988 |
| JP | 5-7492 | 1/1993 |
| JP | 5-93049 | 4/1993 |
| JP | 6-15604 | 3/1994 |
| JP | 7-14352 | 2/1995 |
| JP | 7-265065 | 10/1995 |
| JP | 8-19227 | 2/1996 |
| JP | 2642937 | 5/1997 |
| JP | 9-191893 | 7/1997 |
| JP | 2989175 | 10/1999 |
| JP | 2001-178484 | 7/2001 |
| JP | 2001-288256 | 10/2001 |
| WO | WO 97/07153 A1 | 2/1997 |
| WO | WO 02/16627 A2 | 2/2002 |

OTHER PUBLICATIONS

Katharina Fritzsche et al., "An Unusual Bacterial Polyster with a Phenyl Pendant Group," 191 *Makromol. Chem.* 1957-1965 (1990).

Safwat Antoun et al., "Production of Chiral Polyester by *Pseudomonas oleovorans* Grown with 5-Phenyl-2,4-Pentadienoic Acid," 3(6) *Chirality* 492-494 (1991).

Joanne M. Curley et al., "Production of Poly(3-hydroxyalkanoates) Containing Aromatic Substituents by *Pseudomonas oleovarans*," 29 *Macromol.* 1762-1766 (1996).

Suzette M. Aróstegui et al., "Bacterial Polyesters Produced by *Pseudomonas oleovorans* Containing Nitrophenyl Groups," 32 *Macromol.* 2889-2895 (1999).

Helmut Ritter et al., "Bacterial Production of Polyesters Bearing Phenoxy Groups in the Side Chain, 1 Poly(3-hydroxy-5-phenoxypentanoate-co-3-hydroxy-9-phenoxy-nonanoate) from *Pseudomonas oleovorans*," 195 *Macromol. Chem. Phys.* 1665-1672 (1994).

YoungBaek Kim et al., "Poly-3-hydroxyalkanoates Produced from *Pseudomonas oleovorans* Grown with ω-Polyhydroxyalkanoates," 29 *Macromol.* 3432-3435 (1996).

Ohyoung Kim et al., "Bioengineering of Poly(β-hydroxyalkanoates) for Advanced Material Applications: Incorporation of Cyano and Nitrophenoxy Side Chain Substituents," 41 (Supp. 1) *Can. J. Microbiol.* 32-43 (1995).

Richard A. Gross et al., "Cyanophenoxy-Containing Microbal Polyesters: Structural Analysis, Thermal Properties, Second Harmonic Generation and In-Vivo Biodegradability," 39 *Polymer International* 205-213 (1996).

Marianela Andújar et al., "Polyesters Produced by *Pseudomonal oleovorans* Containing Cyclohexyl Groups," 30 *Macromol.* 1611-1615 (1997).

Won Ho Park et al., "Epoxidation of Bacterial Polyesters with Unsaturated Side Chains. I. Production and Epoxidation of Polyesters From 10-Undecanoic Acid," 31 *Macromol.* 1480-1486 (1998).

Won Ho Park et al., "Epoxidation of Bacterial Polyesters with Unsaturated Side Chains. II. Rate of Epoxidation and Polymer Properties," 36 *J. Polym. Sci.* 2381-2387 (1998).

Yasuo Takagi et al., "Biosynthesis of Polyhydroxyalkanoate with a Thiophenoxy Side Groups Obtained from *Pseudomonas putida*," 32 *Macromol.* 8315-8318 (1999).

Roland G. Lageveen et al., "Formation of Polyesters by *Pseudomonas oleovorans*: Effect of Substrates on Formation and Composition of Poly-(R)-3-Hydroxyalkanoates and Poly-(R)-3-Hydroxyalkenoates," 54(12) *Appl. Environ. Microbiol.* 2924-2932 (1988).

Yoshiharu Doi et al., "Biosynthesis and Characterization of a New Bacterial Copolyester of 3-Hydroxyalkanoates and 3-Hydroxy-ω-Chloroalkanoates," 23 *Macromol.* 3705-3707 (1990).

Kuno Jung et al., "Characterization of New Bacterial Copolyesters Containing 3-Hydroxyalkanoates and Acetoxy-3-Hydroxyalkanoates," 33 *Macromol.* 8571-8575 (2000).

Alan Grund et al., "Regulation of Alkane Oxidation in *Pspeudomonas putida*," 123(2) *J. Bacteriol.* 546-556 (1975).

Katsutoshi Hori et al., "Production of Poly(3-Hydroxyalkanoates-co-3-Hydroxy-ω-Fluoroalkanoates) by *Pseudomonal oleovorans* from 1-Fluorononane and Gluconate," 16(5) *Biotechnol. Lett.* 501-506 (May 1994).

Alexander Steinbüchel et al., "Diversity of Bacterial Polyhydroxyalcanoic Acids," 128 *FEMS Microbiol. Lett.* 219-228 (1995).

C.D. Lytle et al., "Filtration Sizes of Human Immunodeficiency Virus Type 1 and Surrogate Viruses Used to Test Barrier Materials," 58 (2) *Appl. & Environm. Microbiol.* 747-749 (1992).

Richard Ashby et al., "A Tunable Switch to Regulate the Synthesis of Low and High Molecular Weight Microbal Polyesters," 62(1) *Biotechnol. Bioeng.* 106-113 (1999).

Leigh A. Madden et al., "Chain Termination in Polyhydroxyalkanoate Synthesis: Involvement of Exogenous Hydroxy-Compounds as Chain Transfer Agents," 25 *Intl. J. Biol. Macromol.* 43-53 (1999).

Gerhart Braunegg et al., "Polyhydroxyalkanoates, Biopolyesters from Renewable Resources: Physiological and Engineering Aspects," 65 *J. Biotechnol.* 127-161 (1998).

A. Steinbüchel et al., "Molecular Basis for Biosynthesis and Accumulation of Polyhydroxyalkanoic Acids in Bacteria," 103 *FEMS Microbiol. Rev.* 217-230 (1992).

Fengying Shi et al., "Use of Poly(ethylene glycol)s to Regulate Poly(3-hydroxybutyrate) Molecular Weight During *Alcaligenes eutrophus* Cultivations," 29 *Macromol.* 7753-7758 (1996).

Herbert Ulmer et al., "Bacterial Production of Poly(β-hydroxyalkanoates) Containing Unsaturated Repeating Units by *Rhodospirillum rubrum*," 27 *Macromol.* 1675-1679 (1994).

Young B. Kim t al., "Poly(β-hydroxyalkanoate) Copolymers Containing Brominated Repeating Units Produced by *Psudomonas oleovorans*," 25 *Macromol.* 1852-1857 (1992).

Marianela Andújar et al., "Polyesters Produced by *Pseudomonal oleovorans* Containing Cyclohexyl Groups," 30 *Macromol.* 1611-1615 (1997).

J.K. Stille et al., "Tetracyclic Dienes. I. The Diels-Alder Adduct of Norbornadiene and Cyclopentadiene," 81 *J. Am. Chem. Soc.* 4273-4275 (Aug. 1959).

G.J.M. de Koning et al., "A Biodegradable Rubber by Crosslinking Poly(Hydroxyalkanoate) From *Pseudomonas oleovorans*," 35(10) *Polymer* 2090-2097 (1994).

Moon Yeun Lee et al., "Crosslinking of Microbal Copolyesters with Pendant Epoxide Groups by Diamine," 40 *Polymer* 3787-3793 (1999).

M.Y. Lee et al., "Hydrophillic Bacterial Polyesters Modified with Pendant Hydroxyl Groups," 41 *Polymer* 1703-1709 (2000).

Marieta Constantin et al., "Chemical Modification of Poly(hydroxyalkanoates). Copolymers Bearing Pendant Sugars," 20 *Macromol. Rapid Commun.* 91-94 (1999).

\* cited by examiner

METHOD OF PRODUCING POLYHYDROXYALKANOATE FROM ALKANE HAVING RESIDUE CONTAINING AROMATIC RING IN ITS MOLECULE

BACKGROUND OF THE INVENTION

1. Field of the Invention

The present invention relates to a method of producing polyhydroxyalkanoate (may be abbreviated as "PHA" hereinafter) as a polyester by using a substituted alkane derivative as a raw material. More specifically, the present invention relates to a method of producing PHA by using microorganisms having the ability to produce PHA and accumulate it in cells by using a substituted alkane derivative as a raw material.

2. Description of the Related Art

It has been reported that many microorganisms produce poly-3-hydroxybutyric acid (may be abbreviated as "PHB" hereinafter) or other PHAs, and accumulate these polymers in cells ("Biodegradable Plastic Handbook", edited by Society of Biodegradable Plastic Research, N•T•S Co., Ltd., pp. 178–197 (1995)). Like conventional plastics, these polymers can be used for producing various kinds of products by melt processing, and the like. Furthermore, the polymers are biodegradable, and are thus advantageously decomposed completely by microorganisms in nature. Therefore, unlike synthetic polymers, these polymers doe not pollute the environment. The above polymers also have excellent biocompatibility. Thus, it may be expected that they form soft medical materials and like.

It is known that the microorganism producible PHAs have various compositions and structures depending on the types of the microorganisms used for production, culture medium compositions, culture conditions, etc. Therefore, studies have been conducted to control the compositions and structures of PHAs mainly to improve their physical propertie.

For example, it is reported that a strain of *Alcaligenes eutropus* H16 (ATCC No. 17699) or its mutants produce copolymers of 3-hydroxybutyric acid ("3HB") and 3-hydroxyvaleric acid ("3HV") in various composition ratios by using various carbon sources for the culture (Japanese Patent Publication Nos. 6-15604, 7-14352 and 8-19227).

Japanese Patent Publication No. 2642937 discloses that a non-cyclic aliphatic hydrocarbon is added as a carbon source to a strain of *Pseudomonas oleovorans* ATCC 29347 to produce PHA having 3-hydroxyalkanoate having 6 to 12 carbon atoms as a monomer unit.

Japanese Patent Laid-Open No. 5-7492 discloses a method in which microorganisms of *Methylobacterium* sp., *Paracoccus* sp., *Alcaligenes* sp., and *Pseudomonas* sp. are contacted with a primary alcohol having 3 to 7 carbon atoms to produce a copolymer of 3HB and 3HV.

Japanese Patent Laid-Open Nos. 5-93049 and 7-265065 disclose that a strain of *Aeromonas caviae* is cultured with oleic acid and olive oil as carbon sources to produce a binary copolymer of 3HB and 3-hydroxyhexanoic acid ("3HHx").

Japanese Patent Laid-Open No. 9-191893 discloses that a strain of *Comamonas acidovorans* IFO 13852 is cultured with gluconic acid and 1,4-butanediol as carbon sources to produce a polyester having 3HB and 4-hydroxybutyric acid as monomer units.

The above-described PHAs have alkyl groups in side chains, i.e., "usual PHA". However, in considering a wide application of the microorganism producible PHAs, PHAs having substituents other than alky groups, for example, a phenyl group, and the like, which are introduced in side chains, are expected to be useful polyesters. Examples of other substituents include an unsaturated hydrocarbon, an ester group, an allyl group, a cyano group, a halogenated hydrocarbon, an epoxide, and the like. Particularly, PHA having an aromatic ring is extensively studied.

(a) PHA having a phenyl group or partially-substituted phenyl group

In Macromolecules, 24, 5256–5260 (1991), it is reported that *Pseudomonas oleovorans* produces PHA having 3-hydroxy-5-phenylvaleric acid as a unit by using 5-phenylvaleric acid as a substrate.

More specifically, it is reported that *Pseudomonas oleovorans* produces PHA containing 3HV, 3-hydroxyheptanoic acid, 3-hydroxynonanoic acid, 3-hydroxyundecanoic acid, and 3-hydroxy-5-phenylvaleric acid (abbreviated as "3HPV" hereinafter) as monomer units in a ratio of 0.6:16.0:41.1:1.7:40.6 in an amount of 160 mg per liter of culture medium (dry weigh ratio of 31.6% relative to cells) by using 5-phenylvaleric acid (abbreviated as "PVA" hereinafter) and nonanoic acid as substrates (molar ratio, 2:1; total concentration, 10 mmol/L). It is also reported that *Pseudomonas oleovorans* produces PHA containing 3HHx, 3-hydroxyoctanoic acid, 3-hydroxydecanoic acid, and 3HPV as monomer units in a ratio of 7.3:64.5:3.9:24.3 in an amount of 200 mg per liter of culture medium (dry weigh ratio of 39.2% relative to cells) by using PVA and octanoic acid as substrates (molar ratio, 1:1; total concentration, 10 mmol/L).

Besides the above reports, related descriptions are also found in Makromol. Chem., 191, 1957–1965 (1990) and Chirality, 3, 492–494 (1991) in which a change in polymer physical properties due to the presence of a 3HPV unit is recognized.

In Macromolecules, 29, 1762–1766 (1996), it is reported that *Pseudomonas oleovorans* produces PHA having 3-hydroxy-5-(4'-tolyl) valeric acid as a unit by using 5-(4'-tolyl) valeric acid as a substrate.

In Macromolecules, 32, 2889–2895 (1999), it is reported that *Pseudomonas oleovorans* produces PHA having 3-hydroxy-5-(2',4'-dinitrophenyl) valeric acid and 3-hydroxy-5-(4'-nitrophenyl) valeric acid as units by using 5-(2',4'-dinitrophenyl) valeric acid as a substrate.

(b) PHA containing a phenoxy group or a partially-substituted phenoxy group

In Macromol. Chem. Phys., 195, 1665–1672 (1994), it is reported that *Pseudomonas oleovorans* produces a PHA copolymer of 3-hydroxy-5-phenoxy valeric acid and 3-hydroxy-9-phenoxynonanoic acid by using 11-phenoxyundecanoic acid as a substrate.

In Macromolecules, 29, 3432–3435 (1996), it is reported that *Pseudomonas oleovorans* produces PHA containing 3-hydroxy-4-phenoxy-n-burylic aid and 3-hydroxy-6-phenoxy-n-hexanoic acid as units from 6-phenoxyhexanoic acid, PHA containing 3-hydroxy-4-phenoxy-n-butyric acid, 3-hydroxy-6-phenoxy-n-hexanoic acid and 3-hydroxy-8-phenoxy-n-octanoic acid as units from 8-phenxyoctanoic acid, and PHA containing 3-hydroxy-5-phenoxy-n-valeric acid and 3-hydroxy-7-phenoxy-n-heptanoic acid as units from 11-phenoxyundecanoic acid. In this report, the yields of the polymers are extracted and are shown in Table 1.

TABLE 1

| Carbon source (alkanoate) | Dry cell weight (mg/L) | Dry polymer weight (mg/L) | Yield (%) |
|---|---|---|---|
| 6-phenoxyhexanoic acid | 950 | 100 | 10.5 |
| 8-phenoxyoctanoic acid | 820 | 90 | 11 |
| 11-phenoxyundecanoic acid | 150 | 15 | 10 |

Japanese Patent Publication No. 2989175 discloses an invention relating to a homopolymer composed of a 3-hydroxy-5-(monofluorophenoxy)pentanoate (3H5(MFP)P) unit or a 3-hydroxy-5-(difluorophenoxy)pentanoate (3H5(DFP)P) unit, a copolymer comprising at least the 3H5(MFP)P unit or 3H5(DFP)P unit, and a method of producing these polymers by using Pseudomonas putida, Pseudomonas sp. for synthesizing the polymers.

These polymers are produced by the following two-stage culture method.

Culture time: first stage, 24 hours; second stage, 96 hours
The substrate used in each stage and the resultant polymer are shown below.
(1) Resultant polymer: 3-hydroxy-5-(monofluorophenoxy) pentanoate homopolymer
   Substrates in the first stage: citric acid, yeast extract
   Substrate in the second stage: monofluorophenoxy undecanoic acid
(2) Resultant polymer: 3-hydroxy-5-(difluorophenoxy) pentanoate homopolymer
   Substrates in the first stage: citric acid, yeast extract
   Substrate in the second stage: difluorophenoxy undecanoic acid
(3) Resultant polymer: 3-hydroxy-5-(monofluorophenoxy) pentanoate copolymer
   Substrates in the first stage: octanoic acid or nonanoic acid, yeast extract
   Substrate in the second stage: monofluorophenoxy undecanoic acid
(4) Resultant polymer: 3-hydroxy-5-(difluorophenoxy) pentanoate copolymer
   Substrates in the first stage: octanoic acid or nonanoic acid, yeast extract
   Substrate in the second stage: difluorophenoxy undecanoic acid
   For the effect, a polymer having phenoxy groups with side chain terminals substituted by 1 to 2 fluorine atoms can be synthesized by assimilation of a medium-chain fatty acid having substituents, and stereoregularity and water repellency can be imparted to the polymer while maintaining a high melting point and good processability.

Besides the fluorine-substituted polymer, cyano- or nitro-substituted polymers have also be studied.

Can. J. Microbiol., 41, 32–43 (1995) and Polymer International, 39, 205–213 (1996) disclose that PHA containing 3-hydroxy-p-cyanophenoxyhexanoic acid or 3-hydroxy-p-nitrophenoxyhexanoic acid as a monomer unit is produced by using a strain of Pseudomonas oleovorans ATCC 29347 and a strain of Pseudomonas putida KT 2442, and octanoic acid and p-cyanophenoxyhexanoic acid or p-nitrophenoxyhexanoic acid as substrates.

Unlike general PHA having alkyl groups in side chains, the PHA disclosed in this report has aromatic groups in side chains, and thus is advantageous for obtaining a polymer having physical properties derived from the aromatic rings.

(c) PHA having a monomer unit containing a cyclohexyl group is expected to exhibit polymer physical properties different from those of PHA having a monomer unit containing a usual aliphatic hydroxyalkanoic acid. Examples of production with Pseudomonas oleovorans are reported in Macromolecules, 30, 1611–1615 (1997).

In this report, a strain of Pseudomonas oleovorans is cultured in a culture medium containing nonanoic acid and cyclohexyl butyric acid or cyclohexyl valeric acid to obtain PHA having a unit containing a cyclohexyl group and a unit derived from nonanoic acid (the ratio is unknown).

With respect to yield, it is reported that the ratio of nonanoic acid to cyclohexyl butyric acid was changed under the condition of a total substrate concentration of 20 mmol/L to obtain the results shown in Table 2.

TABLE 2

| Nonanoic acid:cyclohexylbutyric acid | CDW | PDW | Yield | Unit |
|---|---|---|---|---|
| 5:5 | 756.0 | 89.1 | 11.8 | nonanoic acid, cyclohexylbutyric acid |
| 1:9 | 132.8 | 19.3 | 14.5 | nonanoic acid, cyclohexylbutyric acid |

CDW: Dry cell weight (mg/L), PDW: Dry polymer weight (mg/L), Yield: PDW/CDW (%)

However, in this example, the polymer yield per liter of culture medium is insufficient, and the resultant PHA itself contains aliphatic hydroxyalkanoic acid derived from nonanoic acid in the monomer unit.

A new category has also been studied, in which PHA having appropriate functional groups in side chains is produced not only for simply changing the physical properties but also for creating a new function by using the functional group.

For example, in Macromolecules, 31, 1480–1486 (1996) and Journal of Polymer Science: Part A; Polymer Chemistry, 36, 2381–2387 (1998), it is reported that PHA having a unit having a vinyl group at a side chain terminal is synthesized, and then epoxidized with an oxidizing agent to synthesize PHA having highly reactive epoxy groups at side chain terminals.

A synthetic example of PHA having a unit containing a sulfide group other than a vinyl group, which is expected to produce high reactivity, is PHA reported in Macromolecules, 32, 8315–8318 (1999) in which a strain of Pseudomonas putida 27N01 produces a PHA copolymer of 3-hydroxy-5-(phenylsulfanyl) valeric acid and 3-hydroxy-7-(phenylsulfanyl) heptanoic acid by using 11-phenylsulfanyl valeric acid as a substrate.

As described above, microorganism producible PHAs having different compositions and structures can be obtained by changing the types of the microorganisms used for production, the medium compositions, and culture conditions. However, the above-described PHAs are produced only for improving physical properties as plastic.

On the other hand, the above-described "unusual PHA" having substituents introduced in side chains can be expected as a "functional polymer" having useful functions and properties due to the properties of the introduced substituents. Therefore, it is thought to be very useful and important to develop an excellent polymer having the above-described function and biodegradability, microorganisms capable of producing the polymer and accumulating the polymer in cells, and a biosynthetic method of effectively producing the polymer with a high purity.

A general method of producing "unusual PHA" having any of various groups introduced in side chains, i.e., PHA having a monomer unit represented by formula (7), with microorganisms comprises chemically synthesizing a substituted fatty acid represented by formula (8), which has a substituent to be introduced, supplying the fatty acid to microorganisms for culture, and then extracting the produced PHA, as disclosed in the above-descried report examples of *Pseudomonas oleovorans*.

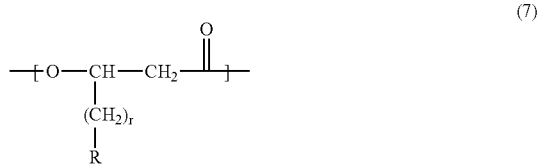
(7)

wherein R represents at least one residue selected from the group consisting of residues each having an aromatic ring, and r represents any integer of 1 to 8.

R—(CH$_2$)s-CH—CH$_2$—COOH     (8)

wherein R represents at least one residue selected from the group consisting of residues each having an aromatic ring, and s represents any integer of 1 to 8.

However, in the above-described general PHA producing method comprising chemically synthesizing the substituted fatty acid as a substrate, and supplying the substituted fatty acid to the microorganisms, a carboxyl group of the substituted fatty acid is an active group in a chemical reaction, and thus chemical synthesis of the fatty acid is greatly restricted according to the type, number and position of the substituents introduced. Therefore, a complicated operation of protecting an active carboxyl group in a reaction step of chemical synthesis, and deprotecting the carboxyl group is frequently required, thereby necessitating a chemical reaction comprising several steps. Therefore, synthesis in an industrial production level is difficult, or synthesis requires much time, labor and cost.

However, if "unusual PHA" can be produced by using as a raw material a substituted alkane that can easily be chemically synthesized, as compared with the substituted fatty acid, the above-described problem can be possibly resolved.

Conventional examples of PHA production from alkane derivatives include examples of biosynthesis of PHA with microorganisms using, as starting materials, straight-chain alkanes and alkenes (alkanes containing double bonds) (Appl. Environ. Microbiol., 54, 2924–2932 (1988)), chlorinated alkanes (Macromolecules, 23, 3705–3707 (1990)), fluorinated alkanes (Biotechnol. Lett., 16, 501–506 (1994)), and alkanes containing acetoxy residues (Macromolecules, 33, 8571–8575 (2000)). There is no report of synthetic examples of PHA using an alkane having a residue containing an aromatic ring as a substituent.

SUMMARY OF THE INVENTION

As a result of intensive research for developing a method of producing "unusual PHA" using a raw material which can easily be synthesized or available, as compared with substituted fatty acids, the inventors found that "unusual PHA" can be produced by using as a raw material a substituted alkane which can easily be chemically synthesized, as compared with substituted fatty acids. This finding resulted in the achievement of a novel PHA producing method using a substituted alkane.

A method of producing polyhydroxyalkanoate by using microorganisms of the present invention comprises culturing microorganisms capable of producing polyhydroxyalkanoate in a medium containing at least one starting compound selected from the group consisting of substituted alkanes represented by formula (1) to produce polyhydroxyalkanoate having, in its molecule, at least one unit selected from the group consisting of 3-hydroxy-substituted alkanoate units represented by formula (2):

R—(CH$_2$)$_n$—CH$_2$—CH$_2$ CH$_3$     (1)

wherein R represents a residue containing a substituted aromatic ring, and n represents any integer of 1 to 8;

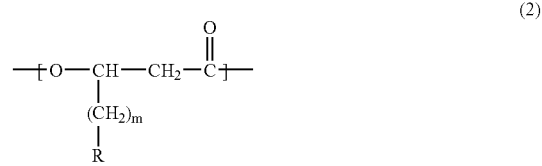
(2)

wherein R represents a residue containing a substituted aromatic ring, and n represents any integer of 1 to 8.

In formulas (1) and (2), a residue R containing a substituted aromatic ring is at least one residue selected from the group consisting of substituted phenylsulfanyl residues represented by formula (3) and the group of consisting of (substituted-phenylmethyl) sulfanyl residues represented by formula (4):

(3)

wherein R1 represents a substituent of an aromatic ring, and is selected from a H atom, a halogen atom, a CN group, a NO$_2$ group, a CH$_3$ group, a C$_2$H$_5$ group, a CH$_3$CH$_2$CH$_2$ group, a (CH$_3$)$_2$CH group, and a (CH$_3$)$_3$C group;

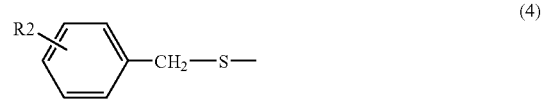
(4)

wherein R2 represents a substituent of an aromatic ring, and is selected from a H atom, a halogen atom, a CN group, a NO$_2$ group, a CH$_3$ group, a C$_2$H$_5$ group, a CH$_3$CH$_2$CH$_2$ group, a (CH$_3$)$_2$CH group, and a (CH$_3$)$_3$C group.

Further objects, features and advantages of the present invention will become apparent from the following description of the preferred embodiments with reference to the attached drawings.

DESCRIPTION OF THE PREFERRED EMBODIMENTS

Figure 1:
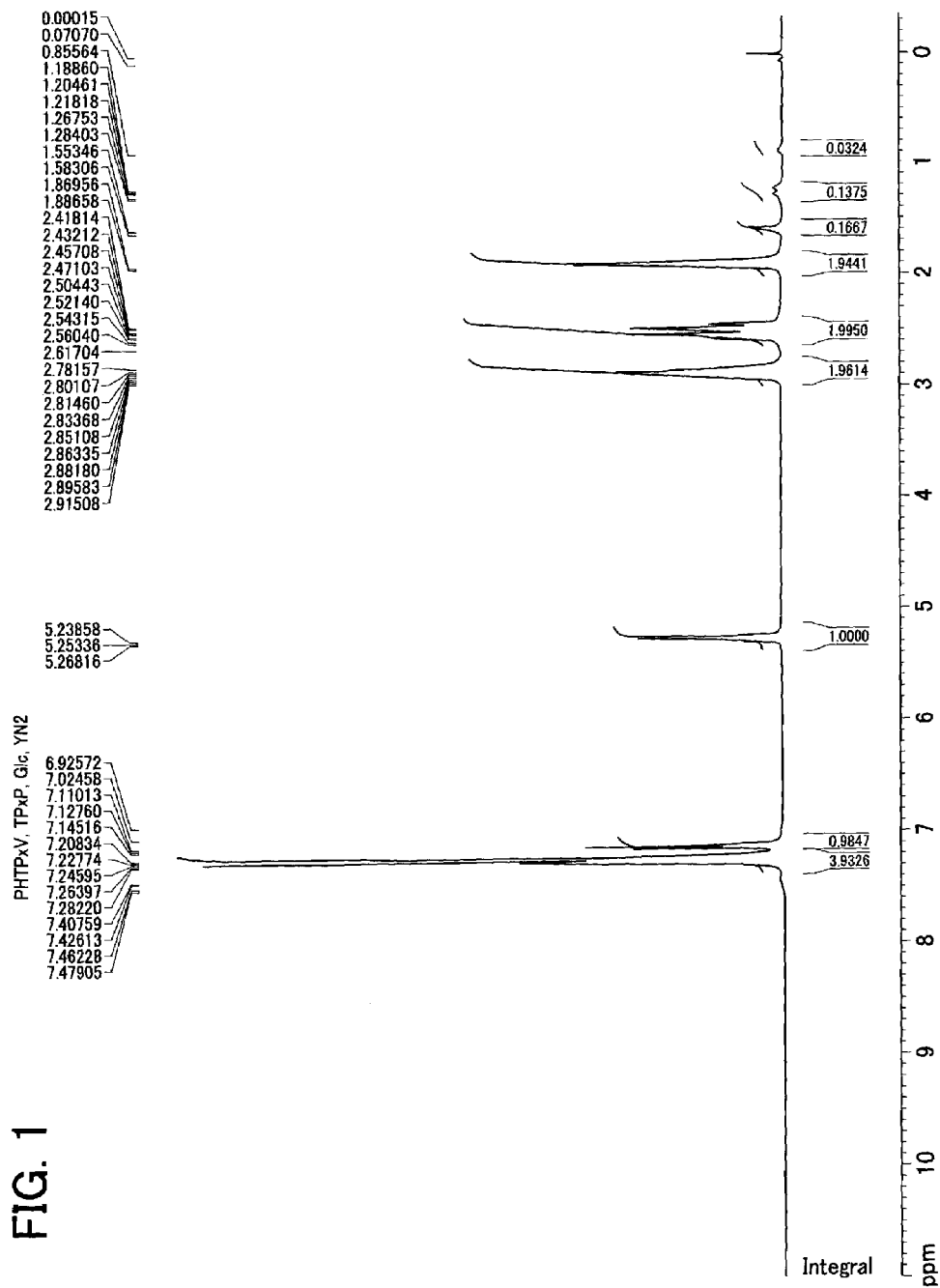
FIG. 1 is a chart showing a 1H-NMR spectrum of polyhydroxyalkanoate produced in Example 1 of the present invention.

As a first example of a compound used as a starting compound in the present invention, at least one compound is selected from 1-[(substituted-phenyl) sulfanyl] alkanes represented by formula (9). In this case, polyhydroxyalkanoate having in its molecule at least one unit selected from 3-hydroxy-ω-[(substituted-phenyl) sulfanyl] alkanoate units represented by formula (10) is produced.

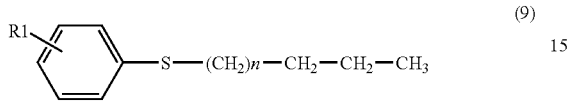

(9)

wherein R1 represents at least one substituent of an aromatic ring, and is selected from a H atom, a halogen atom, a CN group, a $NO_2$ group, a $CH_3$ group, a $C_2H_5$ group, a $CH_3CH_2CH_2$ group, a $(CH_3)_2CH$ group, and a $(CH_3)_3C$ group, and n represents any integer of 1 to 8.

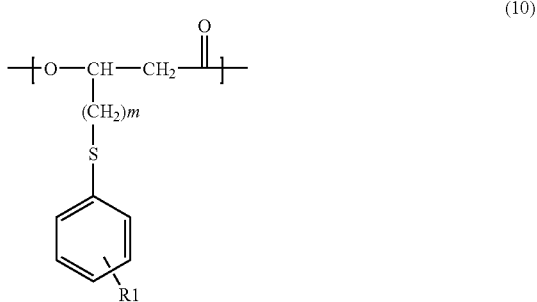

(10)

wherein R1 represents at least one substituent of an aromatic ring, and is selected from a H atom, a halogen atom, a CN group, a $NO_2$ group, a $CH_3$ group, a $C_2H_5$ group, a $CH_3CH_2CH_2$ group, a $(CH_3)_2CH$ group, and a $(CH_3)_3C$ group, and m represents any integer of 1 to 8.

As a second example of a compound used as a starting compound in the present invention, at least one compound is selected from 1-{[(substituted-phenyl)methyl] sulfanyl} alkanes represented by formula (11). In this case, polyhydroxyalkanoate having in its molecule at least one unit selected from 3-hydroxy-ω-{[(substituted-phenyl)methyl] sulfanyl} alkanoate units represented by formula (12) is produced.

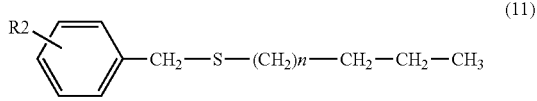

(11)

wherein R2 represents at least one substituent of an aromatic ring, and is selected from a H atom, a halogen atom, a CN group, a $NO_2$ group, a $CH_3$ group, a $C_2H_5$ group, a $CH_3CH_2CH_2$ group, a $(CH_3)_2CH$ group, and a $(CH_3)_3C$ group, and n represents any integer of 1 to 8.

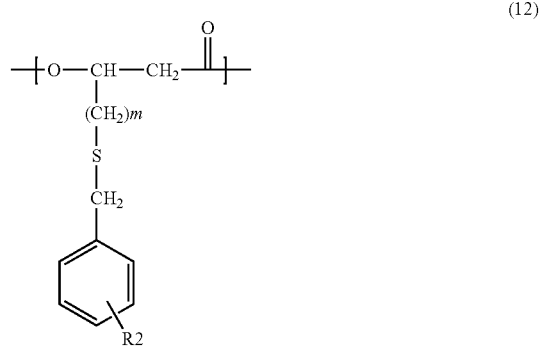

(12)

wherein R2 represents at least one substituent of an aromatic ring, and is selected from a H atom, a halogen atom, a CN group, a $NO_2$ group, a $CH_3$ group, a $C_2H_5$ group, a $CH_3CH_2CH_2$ group, a $(CH_3)_2CH$ group, and a $(CH_3)_3C$ group, and m represents any integer of 1 to 8.

The method of the present invention will be described in detail below. The producing method comprises a step of culturing microorganisms in a medium containing at least one of compounds represented by formula (9) and (11) to produce polyhydroxyalkanoate having in its molecule at least one of 3-hydroxyalkanoic acid units represented by formula (10) and (12).

In the above-described producing method comprising the step of culturing microorganisms, i.e., the step of producing the polyhydroxyalkanoate with microorganisms, the length "n" of a methylene chain of the staring material represented by formula (9) or (11) and the length "m" of a methylene side chain of the unit represented by formula (10) or (12), which is present in the molecule of polyhydroxyalkanoate produced by the method of the present invention, have the following relationship (1):

$$m = n - 2l \quad (1)$$

wherein l is any integer of $0 \leq l < (1/2)n$.

For example, when 7-(phenylsulfanyl) heptane represented by formula (13) is used as the starting material, the produced polyhydroxyalkanoate has a 3-hydroxy-7-(phenylsulfanyl) heptanoic acid unit represented by formula (14), and 3-hydroxy-5-(phenylsulfanyl) valeric acid unit represented by formula (15).

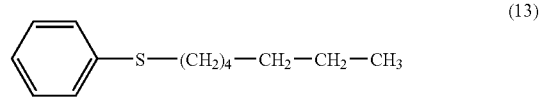

(13)

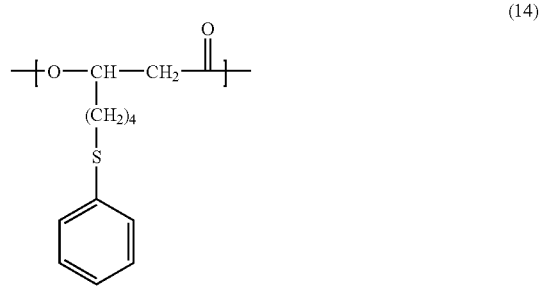

(14)

-continued

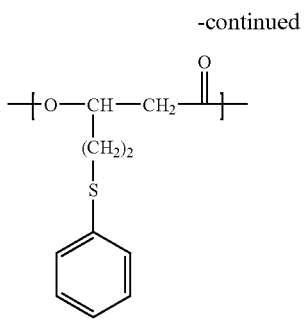

(15)

The PHA produced by the method of the present invention may contain in its polymer molecule at least one unit of 3-hydroxy-alkanoic acid units represented by formula (5):

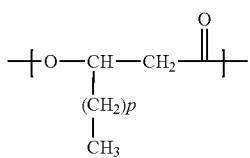

(5)

wherein p represents any integer of 0 to 8, and p may be one or more values in the polymer, or 3-hydroxy-alka-5-ene acid units represented by formula (6):

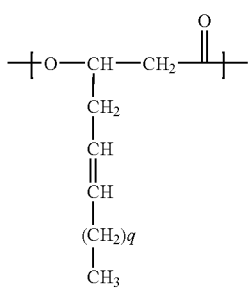

(6)

wherein q represents any integer of 3 to 5, and p may be one or more values in the polymer.

The number-average molecular weight of the PHA produced by the method of the present invention is about 5000 to 1000000.

A description will now be made of the microorganisms, the culturing step and the recovery step in the present invention.

Microorganisms

As the microorganisms used in the method of the present invention, any microorganisms can be used as long as polyhydroxyalkanoate having in its molecule a 3-hydroxy-substituted alkanoate unit represented by formula (2), in which side chains contain a residue having a substituted aromatic ring represented by formula (3) or (4), can be produced by using, as a starting material, i.e., a substrate raw material, a substituted alkane represented by formula (1), which has a residue containing a substituted aromatic ring represented by formula (3) or (4). According to demand, plural types of microorganisms may be used within a range in which the object of the present invention can be achieved.

The microorganisms used in the method of the present invention are required to have at least the ability to convert an alkane into an alkanoic acid, and further have the ability to produce PHA from an alkanoic acid. The ability to convert an alkane into an alkanoic acid is generally exhibited by a group of enzyme systems using alkane monooxygenase as an initiator enzyme.

Microorganisms of *Pseudomonas* sp. are known was the microorganisms used in the present invention. More specifically, examples of the microorganisms include microorganisms isolated from soil, such as microorganisms of *Pseudomonas cichorii* YN2 strain disclosed in Japanese Patent Laid-Open No. 2002-178484, and microorganisms of *Pseudomonas oleovorans* ATCC 29347 strain disclosed in Japanese Patent laid-Open No. 63-226291. The YN strain is deposited as FERM BP-7375 in National Institute of Advanced Industrial Science and Technology, National Institute of Bioscience and Human-Technology.

Culturing Step

In the culturing step of the method of producing polyhydroxyalkanoate (PHA) of the present invention, polyhydroxyalkanoate having in its molecule at least one unit selected from the group consisting of 3-hydroxy-substituted alkanoate units represented by formula (2) is produced from at least one substituted alkane selected from the group consisting of substituted alkanes represented by formula (1) by using the microorganisms having the polyhydroxyalkanoate producing ability.

In order to normally culture the microorganisms used in the culturing step, for example, in order to prepare a stock strain and proliferate the microorganisms for securing the number of the microorganisms necessary for producing PHA and securing an active state thereof, a culture medium containing components necessary for proliferating the microorganisms used is appropriately selected. For example, any culture medium such as a general natural medium (a bouillon medium, a yeast extract, or the like), a synthetic medium containing a source of nutrition, or the like can be used as long as the culture medium has no adverse effect on the growth and survival of the microorganisms. The culture conditions of temperature, aeration, stirring, and the like are appropriately selected according to the microorganisms used.

On the other hand, in the culturing step of producing the target PHA having in its molecule at least one unit selected from the group consisting of 3-hydroxy-substituted alkanoate units represented by formula (1) by using the above-described PHA producing microorganisms, an inorganic culture medium can be used, the culture medium containing, as raw materials for producing the PHA, at least one substituted alkane selected from the group consisting of substituted alkanes represented by formula (1) corresponding to the monomer unit, and a carbon source for proliferating the microorganisms. The initial content of the at least one substituted alkane represented by formula (1) and used as the raw material is preferably selected in the range of 0.01% to 1% (v/v), and more preferably 0.02% to 0.2% (v/v), per liter of culture medium.

As the culturing step, the producing method may comprise a step of culturing the microorganisms in the presence of dicyclopropylketone which is an alkane-oxidation system inducing substance. It is generally known that the alkane-oxidation system is effectively induced by a straight-chain alkane used as a substrate of a metabolic pathway, for example, octane, nonane, or the like. However, when the above-described straight-chain alkane is used as the inducing substance, care must be taken to the phenomenon that the ratio of the medium-chain fatty acid PHA unit in the produced PHA is increased. This is because the straight-chain alkane is converted into a straight-chain alkanoic acid by the alkane oxidation system, and becomes a PHA monomer substrate through a β oxidation system.

The substituted alkane used as the monomer substrate of the present invention also can induce the alkane oxidation system, and can be introduced as a PHA monomer unit like the straight-chain alkane. The alkane oxidation system has been developed as a metabolic system of straight-chain alkane, but the substituted alkane used in the present invention does not sufficiently induce the alkane oxidation system in some cases.

Although dicyclopropylketone functions as an inducting substance in the alkane oxidation system, it does not become the substrate of the oxidation system (it is not oxidized with alkane monooxygenase). Namely, dicyclopropylketone is known as a nonmetabolizable inducing substance (Journal of Bacteriology, 123, 546–556 (1975)). Therefore, in the producing method of the present invention, when the alkane oxidation system is insufficiently induced, when activation is desirably further improved, or when the ratio of a medium chain fatty acid PHA unit in the target PHA is desirably low, dicyclopropylketone can be used as a preferred inducing substance for the alkane oxidation system. In this case, the alkane oxidation system is effectively induced by dicyclopropylketone, and substrate metabolism is completely utilized for converting the substituted alkane used in the present invention. As a result, a monomer unit derived from the substituted alkane can be effectively produced to achieve improvements in the PHA yield and the ratio of the monomer unit derived from the substituted alkane.

Dicyclopropylketone may be added to the culture medium together with the substituted alkane used in the present invention, or singly added to the culture medium. In this case, the content of dicyclopropylketone may be appropriately selected according to conditions such as the type of the proliferation substrate in the culture medium, the presence of the substituted alkane, the concentration of the substituted alkane, the culture type (single-stage culture or multi-stage culture), the stage number of multi-stage culture, etc. However, the content is preferably selected in the range of 0.001% to 1% (v/v), and more preferably 0.01% to 0.1% (v/v), per liter of culture medium.

The substituted alkane represented by formula (1) and used as the raw material is generally hydrophobic, and thus does not necessarily have high water solubility. However, the above-described microorganisms have the property that the substituted alkane can be used as the substrate, and thus even when the amount of the substituted alkane exceeds its solubility to produce a partial suspension portion in an initial stage of culture, the substituted alkane is gradually taken up by the microorganisms during continuous culture, and is thus gradually dissolved in the culture medium, thereby causing no problem. Also, the microorganisms secrete a surfactant-like substance for effectively taking up the substituted alkane, thereby facilitating uptake of the substituted alkane used as the substrate.

In order to improve dispersibility, the substituted alkane represented by formula (1) and used as the substrate may be dissolved in a solvent such as 1-hexadecene or n-hexadecane, or may be added as a fine suspension to the culture medium according to circumferences. In this case, the concentration of the solvent such as 1-hexdecene or n-hexadecane must be 3% (v/v) or less relative to the culture medium.

Furthermore, the proliferation substrate which is used by the microorganisms for proliferation is separately added to the medium. As the proliferation substrate, a nutrient such as a yeast extract, polypeptone or a meat extract can be used. Also, in view of usefulness as a carbon source, the proliferation substrate can be appropriately selected from saccharides, organic acids produced as intermediates in a TCA cycle, organic acids or salts thereof produced in a TCA cycle through a single-stage or two-stage biochemical reaction, amino acids or salts thereof, straight-chain alkanes having 4 to 12 carbons or salts thereof, and the like according to the strain used.

As a saccharide of these proliferation substrates, at least one compound is preferably selected from aldoses such as glyceroaldehyde, erythrose, arabinose, xylose, glucose, galactose, mannose, fructose, and the like; alditols such as glycerol, erythritol, xylitol, and the like; aldonic acids such as gluconic acid, and the like; uronic acids such as glucuronic acid, galacturonic acid, and the like; disaccharides such as maltose, sucrose, lactose, and the like.

As an organic acid or its salt, at least one compound is preferably selected from the group consisting of pyruvic acid, malic acid, lactic acid, citric acid, succinic acid, and salts thereof. As an amino acid or its salt, at least one compound is preferably selected from the group consisting of glutamic acid, asparaginic acid, and salts thereof.

Of the various proliferation substrates, polypentone or a saccharide is preferably used, and particularly, at least one compound is preferably selected from the group consisting of glucose, fructose, and mannose, and used as the saccharide. The content of the proliferation substrate is preferably selected in the range of 0.1% to 5% (w/v), and more preferably in the range of 0.2% to 2% (w/v), per liter of culture medium.

Another method performed in the culturing step of producing and accumulating PHA in the microorganisms comprises sufficiently proliferating the microorganisms, transferring cells to a medium in which a nitrogen source such as ammonium chloride is limited, and then further culturing the cells in a medium containing a compound added as the substrate for the target unit. In this method, productivity may be improved. For example, a multi-step system comprising a plurality of steps performed under different culture conditions may be used.

More specifically, a preferred two-step culture method comprises step 1-1 of culturing the microorganisms in a culture medium containing the substituted alkane represented by formula (1) and a polypeptone as a carbon source until a later stage of exponential growth or a stationary phase and recovering cells by centrifugation, and then step 1-2 of further culturing the cells of the microorganisms, which were cultured and proliferated in the previous step 1-1, in a culture medium containing the substituted alkane represented by formula (1) and an organic acid or its salt as a carbon source and not containing a nitrogen source. Another preferred two-step culturing method comprises step 1-3 of culturing the microorganisms in a culture medium containing the substituted alkane represented by formula (1) and glucose as a carbon source until a later stage of exponential growth or a stationary phase and recovering the cells by centrifugation, and then step 1-4 of further culturing the cells of the microorganisms, which were cultured and proliferated in the previous step 1-3, in a culture medium containing the substituted alkane represented by formula (1) and glucose as a carbon source and not containing a nitrogen source. Still another preferred two-step culture method comprises step 1-5 of culturing the microorganisms in a culture medium containing the substituted alkane represented by formula (1) and a polypeptone as a carbon source until a later stage of exponential growth or a stationary phase and recovering the cells by centrifugation, and then step 1-6 of further culturing the cells of the microorganisms, which were cultured and proliferated in the previous step 1-5, in a culture medium containing the substituted alkane represented by formula (1) and a saccharide as a carbon source and not containing a nitrogen source.

In each of these two-step culture methods, the PHA containing in its molecule at least one unit selected from the group of 3-hydroxy substituted alkanoate units represented by formula (2) is produced from the corresponding substituted alkane represented by formula (1) and used as the raw material during proliferation of the cells in the first step. The cultured cells are then brought into a culture condition mainly for producing the PHA in the medium not containing a nitrogen source in the second step, thereby further increasing the amount of the PHA accumulated in the cells.

Also, dicyclopropylketone, which is an effective inducing substance for the alkane oxidation pathway comprising alkane monooxygenase as an initiator enzyme, can be added in at least one of steps 1-1 and 1-2, steps 1-3 and 1-4, or steps 1-5 and 1-6 to effectively promote metabolism of the substituted alkane to produce the corresponding substituted alkanoic acid, thereby increasing the PHA yield and the ratio of the target PHA monomer unit.

Furthermore, in the first culturing step for mainly inducing the alkane oxidation system, i.e., step 1-1, step 1-3 or step 1-5, dicyclopropylketone may be singly used instead of the substituted alkane.

In the culturing step, the temperature may be set to sufficiently proliferate the strain. For example, the culture temperature is appropriately selected in the range of 15° C. to 40° C., more preferably in the range of 20° C. to 35° C., and most preferably in the range of 20° C. to 30° C.

Any one of a liquid culture method, a solid culture method, and the like may be used as long as the microorganisms used can be proliferated to produce PHA containing in its molecule at least one unit selected from the 3-hydroxy substituted alkanoate units represented by formula (2) from at least one substituted alkane and selected, as the raw material contained in the medium, from the group consisting of substituted alkanes represented by formula (1). Furthermore, any one of batch culture, fed-batch culture, semi-continuous culture, continuous culture, and the like may be used as long as the raw material, the carbon source, and oxygen are properly supplied. Examples of a liquid batch culture method include a method in which oxygen is supplied by shaking a shake flask, and a method in which oxygen is supplied in a stirring aeration system using a jar fermenter.

As the inorganic culture medium used for the culture method, any culture medium can be used as long as it contains components necessary for proliferating the microorganisms, such as a phosphorus source (for example, a phosphate, or the like), a nitrogen source (for example, an ammonium salt, a nitrate, or the like), and the like. For example, a MSB medium or M9 medium can be used.

The composition of the M9 medium used in the method of the present invention is described below.

| | |
|---|---|
| Na$_2$HPO$_4$ | 6.2 g |
| KH$_2$PO$_4$ | 3.0 g |
| NaCl | 0.5 g |
| NH$_4$Cl | 1.0 g |

(per liter of medium, pH 7.0)

In order to further improve proliferation and PHA production, for example, about 0.3% (v/v) of the micro component solvents below must be added for compensating necessary minor elements.

| (Micro component solvent) | |
|---|---|
| Nitrilo-triacetic acid | 1.5 g |
| MgSO$_4$ | 3.0 g |
| MnSO$_4$ | 0.5 g |
| NaCl | 1.0 g |
| FeSO$_4$ | 0.1 g |
| CaCl$_2$ | 0.1 g |
| CoCl$_2$ | 0.1 g |
| ZnSO$_4$ | 0.1 g |
| CuSO$_4$ | 0.1 g |
| AlK(SO$_4$)$_2$ | 0.1 g |
| H$_3$BO$_3$ | 0.1 g |
| Na$_2$MoO$_4$ | 0.1 g |
| NiCl$_2$ | 0.1 g |

(per liter of micro component solvent, pH 7.0)

As the above-described culture method, any one of conventional methods used for culturing microorganisms, such as batch culture, flowing batch culture, semi-continuous culture, continuous culture, reactor-system culture, solid culture, and the like, may be used.

Extraction/Purification Step

A conventional method can be used for obtaining PHA from the microorganism cells, which produce and accumulate it according to the present invention. Recovering PHA from the cultured cells of the microorganisms by extracting with an organic solvent is a simplest method. Examples of the organic solvent include chloroform, dichloromethane, acetone, dioxane, tetrahydrofuran, acetonitrile, and the like.

In an environment where it is difficult to use an organic solvent, a chemical treatment method can be used.

In this case, PHA can be recovered by removing cell components other than PHA by treatment with a surfactant such as SDS, or the like, treatment with an enzyme such as lysozyme, or the like, or treatment with a chemical such as EDTA, ammonia or the like. Also, PHA can be recovered by removing cell components other than PHA with sodium hypochlorite, but the structure may be changed. Furthermore, PHA can be recovered by removing cell components other than PHA by physically crushing the microorganism cells. In this case, any one of methods such s an ultrasonic crushing method, a homogenizer method, a pressure crushing method, a beads impact method, a trituration method, a grinding method, and a freeze thawing method may be used.

In the present invention, culture of the microorganisms, production of PHA using the microorganisms, accumulation of PHA in the cells, and recovery of PHA from the cells are not limited to the above-described methods.

EXAMPLES

Examples of the present invention will be described below. In a description below, "%" is based on mass unless otherwise specified.

Example 1

200 mL of M9 medium containing 0.5% (w/v) of glucose was prepared, placed in a 500 mL shake flask, and then sterilized by an autoclave. After the flask was returned to room temperature, 0.1% (v/v) of 1-(phenylsulfanyl) pentane sterilized with a filter was added to the medium, and well stirred. Then, a *Pseudomonas cichorii* YN2 strain was inoculated into the medium, which was then cultured with shaking at 30° C. at 125 strokes/min. 48 hours thereafter, cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 am, and concentrated with a rotary evaporator, and then the concentrated solution was re-precipitated in cold methanol. Furthermore, only a precipitate was recovered and then vacuum-dried to obtain 96 mg of PHA.

The molecular weight of the thus-obtained PHA was measured by gel permeation chromatography (GPC; Toso HLC-8220, column; Toso TSK-GEL Super HM-H, solvent; chloroform, polystyrene conversion). As a result, Mn=125000 and Mw=278000. The PHA was analyzed by a nuclear magnetic resonance apparatus under the following measurement conditions:

<Measurement apparatus>
  FT-NMR: Bruker DPX400
  Resonance frequency: 1H=400 MHz
<Measurement apparatus>
  Measurement nuclear species: 1H
  Solvent used: $CDCl_3$
  Reference: capillary-sealed $TMS/CDCl_3$
  Measurement temperature: room temperature FIG. 1 is a chart of a 1H-NMR spectrum, and Table 3 shows the results of identification (refer to formula (16)).

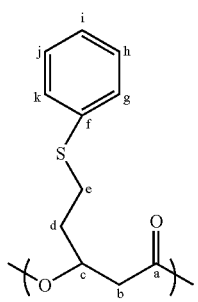

(16)

TABLE 3

| Chemical shift (ppm) | Integral ratio | Split type | Identification result |
|---|---|---|---|
| 1.87 | 2H | m | d |
| 2.41~2.56 | 2H | m | b |
| 2.78~2.91 | 2H | m | e |
| 5.25 | 1H | m | c |
| 6.93~7.14 | 2H | m | i |
| 7.20~7.45 | 5H | m | g, h, j, k |

As shown in Table 3, the PHA was confirmed as PHA containing 97% of 3-hydroxy-5-(phenylsulfanyl) valeric acid unit, and other units comprising saturated or unsaturated 3-hydroxyalkanoic acids having 4 to 12 carbon atoms.

Example 2

200 mL of M9 medium containing 0.5% (w/v) of polypeptone was prepared, placed in a 500 mL shake flask, and then sterilized by an autoclave. After the flask was returned to room temperature, 0.1% (v/v) of 1-(phenylsulfanyl) pentane sterilized with a filter was added to the medium, and well stirred. Then, a *Pseudomonas cichorii* YN2 strain was inoculated into the medium, which was then cultured with shaking at 30° C. at 125 strokes/min. 48 hours thereafter, cells were recovered by centrifugation, washed once with cold methanol, and then freeze-dried.

The freeze-dried pellets were suspended in 20 mL of chloroform, and stirred at 60° C. for 20 hours to extract PHA. The resultant extract was filtered through a membrane filter with a pore size of 0.45 μm, and concentrated with a rotary evaporator. Then, the concentrated solution was re-precipitated in cold methanol. Furthermore, only a precipitate was recovered and then vacuum-dried to obtain 52 mg of PHA.

The molecular weight of the thus-obtained PHA was measured by GPC analysis performed by the same method as in Example 1. As a result, Mn=135000 and Mw=324000. As a result of 1H-NMR analysis of the PHA perfomred by the same method as in Example 1, the PHA was confirmed to contain 63% of a 3-hydroxy-5-(phenylsulfanyl) valeric acid unit and other units comprising saturated or unsaturated 3-hydroxyalkanoic acids having 4 to 12 carbon atoms.

Example 3

200 mL of M9 medium containing 0.5% (w/v) of sodium glutamate were prepared, placed in a 500 mL shake flask and then sterilized by an autoclave. After the flask was returned to room temperature, 0.1% (v/v) of 1-(phenylsulfanyl) pentane sterilized with a filter was added to the medium, and well stirred. Then, a *Pseudomonas cichorii* YN2 strain was inoculated into the medium, which was then cultured with shaking at 30° C. at 125 strokes/min. 48 hours thereafter, cells were recovered by centrifugation, washed once with cold methanol, and then freeze-dried.

The freeze-dried pellets were suspended in 20 mL of chloroform, and stirred at 60° C. for 20 hours to extract the PHA. The resultant extract was filtered through a membrane filter with a pore size of 0.45 μm and concentrated with a rotary evaporator. Then, the concentrated solution was re-precipitated in cold methanol. Furthermore, only a precipitate was recovered and then vacuum-dried to obtain 200 mg of PHA.

The molecular weight of the thus-obtained PHA was measured by GPC analysis performed by the same method as in Example 1. As a result, Mn=122000 and Mw=278000. As a result of 1H-NMR analysis of the PHA performed by the same method as in Example 1, the PHA was confirmed contain 10% of a 3-hydroxy-5-(phenylsulfanyl) valeric acid unit and other units comprising saturated or unsaturated 3-hydroxyalkanoic acids having 4 to 12 carbon atoms.

Example 4

200 mL of M9 medium containing 0.1% (v/v) of nonanoic acid were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, a *Pseudomonas cichorii* YN2 strain was inoculated into the medium, which was then cultured with shaking at 30° C. at 125 strokes/min. 48 hours thereafter, cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm and concentrated with a rotary evaporator. Then, the concentrated solution was re-precipiated in cold methanol. Furthermore, only a precipitate was recovered and then vacuum-dried to obtain 70 mg of PHA.

The molecular weight of the thus-obtained PHA was measured by GPC analysis performed by the same method as in Example 1. As a result, Mn=135000 and Mw=324000. As a result of 1H-NMR analysis of the PHA preformed by the same method as in Example 1, the PHA was confirmed to contain 8% of a 3-hydroxy-5-(phenylsulfanyl) valeric acid unit and other units comprising saturated or unsaturated 3-hydroxyalkanoic acids having 4 to 12 carbon atoms.

Example 5

200 mL of M9 medium containing 0.5% (w/v) of yeast extract were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, a *Pseudomonas cichorii* YN2 strain was inoculated into the medium, which was then cultured with shaking at 30° C. at 125 strokes/min. 48 hours thereafter, cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, and concentrated with a rotary evaporator. Then, the concentrated solution was re-precipitated in cold methanol. Furthermore, only a precipitate was recovered and then vacuum-dried to obtain 45 mg of PHA.

The molecular weight of the thus-obtained PHA was measured by GPC analysis performed by the same method as in Example 1. As a result, Mn=138000 and Mw=331000. As a result of 1H-NMR analysis of the PHA performed by the same method as in Example 1, the PHA was confirmed to contain 61% of a 3-hydroxy-5-(phenylsulfanyl) valeric acid unit and other units comprising saturated/unsaturated 3-hydroxyalkanoic acids having 4 to 12 carbon atoms.

Example 6

200 mL of M9 medium containing 0.5% (w/v) of glucose were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, a *Pseudomonas cichorii* YN2 strain was inoculated into the medium, which was then cultured with shaking at 30° C. at 125 strokes/min. Then, when a turbidity of the culture medium at 600 nm was 0.1, 0.05% (v/v) of dicyclopropylketone was further added to the culture medium and well stirred. After culture with shaking was continued for 90 hours, cells were recovered by centrifugation, washed once with cold methanol, and then freeze-dried.

The freeze-dried pellets were suspended in 20 mL of chloroform, and stirred at 60° C. for 20 hours to extract the PHA. The resultant extract was filtered through a membrane filter with a pore size of 0.45 μm, and concentrated with a rotary evaporator. Then, the concentrated solution was re-precipitated in cold methanol. Furthermore, only a precipitate was recovered and then vacuum-dried to obtain 65 mg of PHA.

The molecular weight of the thus-obtained PHA was measured by GPC analysis performed by the same method as in Example 1. As a result, Mn=121000 and Mw=281000. As a result of 1H-NMR analysis of the PHA performed by the same method as in Example 1, the PHA was confirmed to contain 92% of a 3-hydroxy-5-(phenylsulfanyl) valeric acid unit and other units comprising saturated or unsaturated 3-hydroxyalkanoic acids having 4 to 12 carbon atoms.

Example 7

200 mL of M9 medium containing 0.5% (w/v) of polypeptone were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, a *Pseudomonas cichorii* YN2 strain was inoculated into the medium, which was then cultuered with shaking at 30° C. at 125 strokes/min. Then, when a turbidity of the culture medium at 600 nm was 0.1, 0.05% (v/v) of dicyclopropylketone was further added to the culture medium and well stirred. After culturing with shaking for 48 hours, cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, concentrated with a rotary evaporator, and then the concentrated solution was re-precipitated in cold methanol. Furthermore, only a precipitate was recovered and then vacuum-dried to obtain 58 mg of PHA.

The molecular weight of the thus-obtained PHA was measured by GPC analysis performed by the same method as in Example 1. As a result, Mn=108000 and Mw=245000. As a result of 1H-NMR analysis of the PHA performed by the same method as in Example 1, the PHA was confirmed as PHA containing 70% of 3-hydroxy-5-(phenylsulfanyl) valeric acid unit, and other units comprising saturated or unsaturated 3-hydroxyalkanoic acids having 4 to 12 carbon atoms.

Example 8

200 mL of M9 medium containing 0.5% (w/v) of glucose was prepared, placed in a 500 mL shake flask, and then sterilized by an autoclave. After the flask was returned to room temperature, 0.1% (v/v) of 1-(phenylsulfanyl) pentane sterilized with a filter was added to the medium, and well stirred. Then, a *Pseudomonas cichorii* YN2 strain was inoculated into the medium, which was then cultured with shaking at 30° C. at 125 strokes/min. 90 hours thereafter, cells were recovered by centrifugation.

Next, 200 mL of M9 medium containing 0.5% (w/v) of glucose and not containing $NH_4Cl$ as a nitrogen source was prepared, placed in a 500 mL shake flask, and then sterilized by an autoclave. After the flask was returned to room temperature, 0.1% (v/v) of 1-(phenylsulfanyl) pentane sterilized with a filter was added to the medium, and well stirred.

Then, the recovered cells were again suspended in the medium, and shaking culture was performed at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm and concentrated with a rotary evaporator. Then, the concentrated solution was re-precipitated in cold methanol. Furthermore, only a precipitate was recovered and then vacuum-dried to obtain 125 mg of PHA.

The molecular weight of the thus-obtained PHA was measured by GPC analysis performed by the same method as in Example 1. As a result, Mn=125000 and Mw=272000. As a result of 1H-NMR analysis of the PHA performed by the same method as in Example 1, the PHA was confirmed to contain 87% of a 3-hydroxy-5-(phenylsulfanyl) valeric acid unit and other units comprising saturated or unsaturated 3-hydroxyalkanoic acids having 4 to 12 carbon atoms.

Example 9

200 mL of M9 medium containing 0.5% (w/v) of glucose were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, a *Pseudomonas cichorii* YN2 strain was inoculated into the medium, which was then cultured with shaking at 30° C. at 125 strokes/min. 90 hours thereafter, cells were recovered by centrifugation.

Next, 200 mL of M9 medium containing 0.5% (w/v) of glucose were prepared, placed in a 500 mL shake flask, and then sterilized by an autoclave. After the flask was returned to room temperature, 1-(phenylsulfanyl) pentane sterilized with a filter was added to the medium so that the concentration was 0.1% (v/v) and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm and concentrated with a rotary evaporator. Then, the concentrated solution was re-precipitated in cold methanol. Furthermore, only a precipitate was recovered and then vacuum-dried to obtain 147 mg of PHA.

The molecular weight of the thus-obtained PHA was measured by GPC analysis performed by the same method as in Example 1. As a result, Mn=129000 and Mw=286000. As a result of 1H-NMR analysis of the PHA performed by the same method as in Example 1, the PHA was confirmed to contain 89% of a 3-hydroxy-5-(phenylsulfanyl) valeric acid unit and other units comprising saturated or unsaturated 3-hydroxyalkanoic acids having 4 to 12 carbon atoms.

Example 10

200 mL of M9 medium containing 0.5% (w/v) of glucose was prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, a *Pseudomonas cichorii* YN2 strain was inoculated into the medium, which was then cultured with shaking at 30° C. at 125 strokes/min. 90 hours thereafter, cells were recovered by centrifugation.

Next, 200 mL of M9 medium not containing NH$_4$Cl as a nitrogen source were prepared, placed in a 500 mL shake flask, and then sterilized by an autoclave. After the flask was returned to room temperature, 0.1% (v/v) of 1-(phenylsulfanyl) pentane sterilized with a filter was added to the medium, and well stirred. Then, the recovered cells were again suspended in the medium, and shaking culture was performed at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm and concentrated with a rotary evaporator. Then, the concentrated solution was re-precipitated in cold methanol. Furthermore, only a precipitate was recovered and then vacuum-dried to obtain 70 mg of PHA.

The molecular weight of the thus-obtained PHA was measured by GPC analysis performed by the same method as in Example 1. As a result, Mn=138000 and Mw=298000. As a result of 1H-NMR analysis of the PHA performed by the same method as in Example 1, the PHA was confirmed to contain 96% of a 3-hydroxy-5-(phenylsulfanyl) valeric acid unit and other units comprising saturated or unsaturated 3-hydroxyalkanoic acids having 4 to 12 carbon atoms.

Example 11

200 mL of M9 medium containing 0.5% (w/v) of glucose were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, a *Pseudomonas cichorii* YN2 strain was inoculated into the medium, which was then cultuered with shaking at 30° C. at 125 strokes/min. When a turbidity of the culture medium at 600 nm was 0.1, 0.05% (v/v) of dicyclopropylketone was further added to the culture medium and well stirred. After the shaking culture was continued for 14 hours, cells were recovered by centrifugation.

Next, 200 mL of M9 medium containing 0.5% (v/v) of glucose and not containing NH$_4$Cl as a nitrogen source were prepared, placed in a 500 mL shake flask, and then sterilized by an autoclave. After the flask was returned to room temperature, 0.1% (v/) of 1-(phenylsulfanyl) pentane sterilized with a filter and 0.05% (v/v) of dicyclopropylketone were added to the medium and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm and concentrated with a rotary evaporator. Then, the concentrated solution was re-precipitated in cold methanol. Furthermore, only a precipitate was recovered and then vacuum-dried to obtain 8 mg of PHA.

The molecular weight of the thus-obtained PHA was measured by GPC analysis performed by the same method as in Example 1. As a result, Mn=128000 and Mw=278000. As a result of 1H-NMR analysis of the PHA performed by the same method as in Example 1, the PHA was confirmed to contain 94% of a -hydroxy-5-(phenylsulfanyl) valeric acid unit and other units comprising saturated or unsaturated 3-hydroxyalkanoic acids having 4 to 12 carbon atoms.

Example 12

200 mL of M9 medium containing 0.5% (w/v) of glucose were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, a *Pseudomonas cichorii* YN2 strain was inoculated into the medium, which was then cultured with shaking at 30° C. at 125 strokes/min. When a turbidity of the culture medium at 600 nm was 0.1, 0.05% (v/v) of dicyclopropylketone was further added to the culture medium and well stirred. After culturing with shaking was continued for 14 hours, cells were recovered by centrifugation.

Next, 200 mL of M9 medium containing 0.5% (w/v) of glucose and not containing $NH_4Cl$ as a nitrogen source was prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm and concentrated with a rotary evaporator. Then, the concentrated solution was re-precipitated in cold methanol. Furthermore, only a precipitate was recovered and then vacuum-dried to obtain 14 mg of PHA.

The molecular weight of the thus-obtained PHA was measured by GPC analysis performed by the same method as in Example 1. As a result, Mn=125000 and Mw=282000. As a result of 1H-NMR analysis of the PHA performed by the same method as in Example 1, the PHA was confirmed to contain 88% of a 3-hydroxy-5-(phenylsulfanyl) valeric acid unit and other units comprising saturated or unsaturated 3-hydroxyalkanoic acids having 4 to 12 carbon atoms.

Example 13

200 mL of M9 medium containing 0.5% (w/v) of glucose were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, a *Pseudomonas cichorii* YN2 strain was inoculated into the medium, which was then cultured with shaking at 30° C. at 125 strokes/min. When a turbidity of the culture medium at 600 nm was 0.1, 0.05% (v/v) of dicyclopropylketone was further added to the culture medium and well stirred. After the shaking culture was continued for 14 hours, cells were recovered by centrifugation.

Next, 200 mL of M9 medium containing 0.5% (w/v) of glucose were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm and concentrated with a rotary evaporator. Then, the concentrated solution was re-precipitated in cold methanol. Furthermore, only a precipitate was recovered and then vacuum-dried to obtain 90 mg of PHA.

The molecular weight of the thus-obtained PHA was measured by GPC Analysis performed by the same method as in Example 1. As a result, Mn=138000 and Mw=298000. As a result of 1H-NMR analysis of the PHA performed by the same method as in Example 1, the PHA was confirmed to contain 90% of a 3-hydroxy-5-(phenylsulfanyl) valeric acid unit and other units comprising saturated or unsaturated 3-hydroxyalkanoic acids having 4 to 12 carbon atoms.

Example 14

200 mL of M9 medium containing 0.5% (w/v) of glucose were prepared, placed in a 500 mL shake flask, and then sterilized by an autoclave. After the flask was returned to room temperature, a *Pseudomonas cichorii* YN2 strain was inoculated into the medium, which was then cultured with shaking at 30° C. at 125 strokes/min. When a turbidity of the culture medium at 600 nm was 0.1, 0.05% (v/v) of dicyclopropylketone was added to the medium and well stirred. After the shaking culture was continued for 14 hours, cells were recovered by centrifugation.

Next, 200 mL of M9 medium containing 0.5% (w/v) of glucose was prepared, placed in a 500 mL shake flask, and then sterilized by an autoclave. After the flask was returned to room temperature, 0.1% (v/v) of 1-(phenylsulfanyl) pentane sterilized with a filter and 0.05% (v/v) of dicyclopropylketone were added to the medium and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm and concentrated with a rotary evaporator. Then, the concentrated solution was re-precipitated in cold methanol. Furthermore, only a precipitate was recovered and then vacuum-dried to obtain 51 mg of PHA.

The molecular weight of the thus-obtained PHA was measured by GPC analysis performed by the same method as in Example 1. As a result, Mn=121000 and Mw=283000. As a result of 1H-NMR analysis of the PHA performed by the same method as in Example 1, the PHA was confirmed to contain 80% of a 3-hydroxy-5-(phenylsulfanyl) valeric acid unit and other units comprising saturated or unsaturated 3-hydroxyalkanoic acids having 4 to 12 carbon atoms.

Example 15

200 mL of M9 medium containing 0.5% (w/v) of glucose were prepared, placed in a 500 mL shake flask, and then sterilized by an autoclave. After the flask was returned to room temperature, a *Pseudomonas cichorii* YN2 strain was inoculated into the medium, which was then cultured with shaking at 30° C. at 125 strokes/min. When a turbidity of the culture medium at 600 nm was 0.1, 0.05% (v/v) of dicyclopropylketone was added to the medium and well stirred. After the shaking culture was continued for 14 hours, cells were recovered by centrifugation.

Next, 200 mL of M9 medium containing 0.5% (w/v) of glucose and not containing $NH_4Cl$ as a nitrogen source was prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, the recovered cells were again suspended in the medium, and shaking culture was performed at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, and concentrated with a rotary evaporator, and then the concentrated solution was re-precipitated in cold methanol. Furthermore, only a precipitate was recovered and then vacuum-dried to obtain 14 mg of PHA.

The molecular weight of the thus-obtained PHA was measured by GPC analysis performed by the same method as in Example 1. As a result, Mn=119000 and Mw=245000. As a result of 1H-NMR analysis of the PHA performed by the same method as in Example 1, the PHA was confirmed to contain 89% of a 3-hydroxy-5-(phenylsulfanyl) valeric acid unit and other units comprising saturated or unsaturated 3-hydroxyalkanoic acids having 4 to 12 carbon atoms.

Example 16

200 mL of M9 medium containing 0.5% (w/v) of glucose were prepared, placed in a 500 mL shake flask, and then sterilized by an autoclave. After the flask was returned to room temperature, a *Pseudomonas cichorii* YN2 strain was inoculated into the medium, which was then cultured with shaking at 30° C. at 125 strokes/min. When a turbidity of the culture medium at 600 nm was 0.1, 0.05% (v/v) of dicyclopropylketone was added to the medium and well stirred. After being cultured with shaking for 14 hours, cells were recovered by centrifugation.

Next, 200 mL of M9 medium containing 0.5% (w/v) of glucose were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm and concentrated with a rotary evaporator. Then, the concentrated solution was re-precipitated in cold methanol. Furthermore, only a precipitate was recovered and then vacuum-dried to obtain 65 mg of PHA.

The molecular weight of the thus-obtained PHA was measured by GPC analysis performed by the same method as in Example 1. As a result, Mn=137000 and Mw=299000. As a result of 1H-NMR analysis of the PHA performed by the same method as in Example 1, the PHA was confirmed to contain 72% of a 3-hydroxy-5-(phenylsulfanyl) valeric acid unit and other units comprising saturated or unsaturated 3-hydroxyalkanoic acids having 4 to 12 carbon atoms.

Example 17

200 mL of M9 medium containing 0.5% (w/v) of glucose were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, a *Pseudomonas cichorii* YN2 strain was inoculated into the medium, which was then cultuerd with shaking at 30° C. at 125 strokes/min. When a turbidity of the culture medium at 600 nm was 0.1, 0.05% (v/v) of dicyclopropylketone was further added to the medium and well stirred. After shaking culture was continued for 14 hours, cells were recovered by centrifugation.

Next, 200 mL of M9 medium containing 0.5% (w/v) of glucose and not containing $NH_4Cl$ as a nitrogen source were prepared, placed in a 500 mL shake flask, and then sterilized by an autoclave. After the flask was returned to room temperature, 0.1% (v/v) of 1-(phenylsulfanyl) pentane sterilized with a filter and 0.05% (v/v) of dicyclopropylketone were added to the medium and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm and concentrated with a rotary evaporator. Then, the concentrated solution was re-precipitated in cold methanol. Furthermore, only a precipitate was recovered, and then vacuum-dried to obtain 5 mg of PHA.

The molecular weight of the thus-obtained PHA was measured by GPC analysis performed by the same method as in Example 1. As a result, Mn=118000 and Mw=262000. As a result of 1H-NMR analysis of the PHA performed by the same method as in Example 1, the PHA was confirmed to contain 89% of a 3-hydroxy-5-(phenylsulfanyl) valeric acid unit and other units comprising saturated or unsaturated 3-hydroxyalkanoic acids having 4 to 12 carbon atoms.

Example 18

200 mL of M9 medium containing 0.5% (w/v) of glucose were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, a *Pseudomonas cichorii* YN2 strain was inoculated into the medium, which was then cultured with shaking at 30° C. at 125 strokes/min. When a turbidity of the culture medium at 600 nm was 0.1, 0.05% (v/v) of dicyclopropylketone was added further added to the medium and well stirred. After shaking culture was continued for 14 hours, cells were recovered by centrifugation.

Next, 200 mL of M9 medium containing 0.5% (w/v) of glucose were prepared, placed in a 500 mL shake flask, and then sterilized by an autoclave. After the flask was returned to room temperature, 0.1% (v/v) of 1-(phenylsulfanyl) pentane sterilized with a filter and 0.05% (v/v) of dicyclopropylketone were added to the medium and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 µm and concentrated with a rotary evaporator. Then, the concentrated solution was re-precipitated in cold methanol. Furthermore, only a precipitate was recovered, and then vacuum-dried to obtain 60 mg of PHA.

The molecular weight of the thus-obtained PHA was measured by GPC analysis performed by the same method as in Example 1. As a result, Mn=110000 and Mw=262000. As a result of 1H-NMR analysis of the PHA performed by the same method as in Example 1, the PHA was confirmed to contain 78% of a 3-hydroxy-5-(phenylsulfanyl) valeric acid unit, and other units comprising saturated or unsaturated 3-hydroxyalkanoic acids having 4 to 12 carbon atoms.

Example 19

200 mL of M9 medium containing 0.5% (w/v) of glucose were prepared, placed in a 500 mL shake flask, and then sterilized by an autoclave. After the flask was returned to room temperature, a *Pseudomonas cichorii* YN2 strain was inoculated into the medium, which was then cultured with shaking at 30° C. at 125 strokes/min. When a turbidity of the culture medium at 600 nm was 0.1, 0.05% (v/v) of dicyclopropylketone was added to the medium and well stirred. After the shaking culture was continued for 14 hours, cells were recovered by centrifugation.

Next, 200 mL of M9 medium containing 0.5% (w/v) of glucose and not containing $NH_4Cl$ as a nitrogen source were prepared, placed in a 500 mL shake flask, and then sterilized by an autoclave. After the flask was returned to room temperature, 0.1% (v/v) of 1-(phenylsulfanyl) pentane sterilized with a filter and 0.05% (v/v) of dicyclopropylketone were added to the medium, and well stirred. Then, the recovered cells were again suspended in the medium, and shaking culture was performed at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 µm and concentrated with a rotary evaporator. Then, the concentrated solution was re-precipitated in cold methanol. Furthermore, only a precipitate was recovered and then vacuum-dried to obtain 8 mg of PHA.

The molecular weight of the thus-obtained PHA was measured by GPC analysis performed by the same method as in Example 1. As a result, Mn=121000 and Mw=278000. As a result of 1H-NMR analysis of the PHA performed by the same method as in Example 1, the PHA was confirmed to contain 89% of a 3-hydroxy-5-(phenylsulfanyl) valeric acid unit and other units comprising saturated or unsaturated 3-hydroxyalkanoic acids having 4 to 12 carbon atoms.

Example 20

200 mL of M9 medium containing 0.5% (w/v) of glucose were prepared, placed in a 500 mL shake flask, and then sterilized by an autoclave. After the flask was returned to room temperature, a *Pseudomonas cichorii* YN2 strain was inoculated into the medium, which was then cultured with shaking at 30° C. at 125 strokes/min. When a turbidity of the culture medium at 600 nm was 0.1, 0.05% (v/v) of dicyclopropylketone was added to the medium and well stirred. After being cultured with shaking for 14 hours, cells were recovered by centrifugation.

Next, 200 mL of M9 medium containing 0.5% (w/v) of glucose were prepared, placed in a 500 mL shake flask, and then sterilized by an autoclave. After the flask was returned to room temperature, 0.1% (v/v) of 1-(phenylsulfanyl) pentane sterilized with a filter and 0.05% (v/v) of dicyclopropylketone were added to the medium and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 µm and concentrated with a rotary evaporator. Then, the concentrated solution was re-precipitated in cold methanol. Furthermore, only a precipitate was recovered and then vacuum-dried to obtain 30 mg of PHA.

The molecular weight of the thus-obtained PHA was measured by GPC analysis performed by the same method as in Example 1. As a result, Mn=122000 and Mw=269000. As a result of 1H-NMR analysis of the PHA performed by the same method as in Example 1, the PHA was confirmed to contain 72% of a 3-hydroxy-5-(phenylsulfanyl) valeric acid unit and other units comprising saturated or unsaturated 3-hydroxyalkanoic acids having 4 to 12 carbon atoms.

Example 21

200 mL of M9 medium containing 0.5% (w/v) of polypeptone were prepared, placed in a 500 mL shake flask, and then sterilized by an autoclave. After the flask was returned to room temperature, 0.1% (v/v) of 1-(phenylsulfanyl) pentane sterilized with a filter was added to the culture medium, and well stirred. Then, a *Pseudomonas cichorii* YN2 strain was inoculated into the culture medium, which was then cultured with shaking at 30° C. at 125 strokes/min. After the shaking culture was continued for 48 hours, cells were recovered by centrifugation.

Next, 200 mL of M9 medium containing 0.5% (w/v) of glucose and not containing $NH_4Cl$ as a nitrogen source was prepared, placed in a 500 mL shake flask, and then sterilized by an autoclave. After the flask was returned to room temperature, 0.1% (v/v) of 1-(phenylsulfanyl) pentane sterilized with a filter was added to the medium, and well stirred. Then, the recovered cells were again suspended in the medium, which was then cultured with shaking at 30° C. at 125 strokes/min. 90 hours thereafter, the cells were recovered by centrifugation, washed once with cold methanol and then freeze-dried.

The freeze-dried pellets were suspended in 20 mL of chloroform and stirred at 60° C. for 20 hours to extract the PHA. The resultant extract was filtered through a membrane filter with a pore size of 0.45 am, and concentrated with a rotary evaporator, and then the concentrated solution was re-precipitated in cold methanol. Furthermore, only a precipitate was recovered and then vacuum-dried to obtain 121 mg of PHA.

The molecular weight of the thus-obtained PHA was measured by GPC analysis performed by the same method as in Example 1. As a result, Mn=121000 and Mw=278000. As a result of 1H-NMR analysis of the PHA performed by the same method as in Example 1, the PHA was confirmed to contain 94% of a 3-hydroxy-5-(phenylsulfanyl) valeric acid unit and other units comprising saturated or unsaturated 3-hydroxyalkanoic acids having 4 to 12 carbon atoms.

Example 22

200 mL of M9 medium containing 0.5% (w/v) of polypeptone were prepared, placed in a 500 mL shake flask, and then sterilized by an autoclave. After the flask was returned to room temperature, 0.1% (v/v) of 1-(phenylsulfanyl) pentane sterilized with a filter was added to the culture medium and well stirred. Then, a *Pseudomonas cichorii* YN2 strain was inoculated into the culture medium, which was then cultured with shaking at 30° C. at 125 strokes/min. After the shaking culture was continued for 48 hours, cells were recovered by centrifugation.

Next, 200 mL of M9 medium containing 0.5% (w/v) of glucose were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, concentrated with a rotary evaporator, and then the concentrated solution was re-precipitated in cold methanol. Furthermore, only a precipitate was recovered and then vacuum-dried to obtain 115 mg of PHA.

The molecular weight of the thus-obtained PHA was measured by GPC analysis performed by the same method as in Example 1. As a result, Mn=121000 and Mw=282000. As a result of 1H-NMR analysis of the PHA performed by the same method as in Example 1, the PHA was confirmed to contain 93% of a -hydroxy-5-(phenylsulfanyl) valeric acid unit and other units comprising saturated or unsaturated 3-hydroxyalkanoic acids having 4 to 12 carbon atoms.

Example 23

200 mL of M9 medium containing 0.5% (w/v) of polypeptone were prepared, placed in a 500 mL shake flask, and then sterilized by an autoclave. After the flask was returned to room temperature, 0.1% (v/v) of 1-(phenylsulfanyl) pentane sterilized with a filter was added to the medium, and well stirred. Then, a *Pseudomonas cichorii* YN2 strain was inoculated into the medium, which was then cultured with shaking at 30° C. at 125 strokes/min. After the shaking culture was continued for 48 hours, cells were recovered by centrifugation.

Next, 200 mL of M9 medium not containing NH$_4$Cl as a nitrogen source were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, the recovered cells were again suspended in the medium, which was then cultured with shaking at 30° C. at 125 strokes/min. 90 hours thereafter, the cells were recovered by centrifugation, washed once with cold methanol and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, concentrated with a rotary evaporator, and then the concentrated solution was re-precipitated in cold methanol. Furthermore, only a precipitate was recovered and then vacuum-dried to obtain 51 mg of PHA.

The molecular weight of the thus-obtained PHA was measured by GPC analysis performed by the same method as in Example 1. As a result, Mn=119000 and Mw=278000. As a result of 1H-NMR analysis of the PHA performed by the same method as in Example 1, the PHA was confirmed to contain 96% of a 3-hydroxy-5-(phenylsulfanyl) valeric acid unit and other units comprising saturated or unsaturated 3-hydroxyalkanoic acids having 4 to 12 carbon atoms.

Example 24

200 mL of M9 medium containing 0.5% (w/v) of polypeptone were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, a *Pseudomonas cichorii* YN2 strain was inoculated into the medium, which was then cultured with shaking at 30° C. at 125 strokes/min. When a turbidity of the culture medium at 600 nm was 0.1, 0.05% (v/v) of dicyclopropylketone was further added to the medium, and well stirred. After being cultured with shaking for 14 hours, cells were recovered by centrifugation.

Next, 200 mL of M9 medium containing 0.5% (w/v) of glucose and not containing NH$_4$Cl as a nitrogen source were prepared, placed in a 500 mL shake flask, and then sterilized by an autoclave. After the flask was returned to room temperature, 0.1% (v/v) of 1-(phenylsulfanyl) pentane sterilized with a filter was added to the medium, and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, concentrated with a rotary evaporator, and then the concentrated solution was re-precipitated in cold methanol. Furthermore, only a precipitate was recovered and then vacuum-dried to obtain 160 mg of PHA.

The molecular weight of the thus-obtained PHA was measured by GPC analysis performed by the same method as in Example 1. As a result, Mn=140000 and Mw=308000. As a result of 1H-NMR analysis of the PHA performed by the same method as in Example 1, the PHA was confirmed to contain 85% of a 3-hydroxy-5-(phenylsulfanyl) valeric acid unit and other units comprising saturated or unsaturated 3-hydroxyalkanoic acids having 4 to 12 carbon atoms.

Example 25

200 mL of M9 medium containing 0.5% (w/v) of polypeptone were prepared, placed in a 500 mL shake flask, and then sterilized by an autoclave. After the flask was returned to room temperature, 0.1% (v/v) of 1-(phenylsulfanyl) pentane sterilized with a filter was added to the medium, and well stirred. Then, a *Pseudomonas cichorii* YN2 strain was inoculated into the medium, which was then cultured with shaking at 30° C. at 125 strokes/min. When a turbidity of the culture medium at 600 nm was 0.1, 0.05% (v/v) of dicyclopropylketone was further added to the medium, and well stirred. After the shaking culture was continued for 14 hours, cells were recovered by centrifugation.

Next, 200 mL of M9 medium containing 0.5% (w/v) of glucose was prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, the recovered cells were again suspended in the medium, which was then cultured with at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, concentrated with a rotary evaporator, and then the concentrated solution was re-precipitated in cold methanol. Furthermore, only a precipitate was recovered and then vacuum-dried to obtain 118 mg of PHA.

The molecular weight of the thus-obtained PHA was measured by GPC analysis performed by the same method as in Example 1. As a result, Mn=138000 and Mw=312000. As a result of 1H-NMR analysis of the PHA performed by the same method as in Example 1, the PHA was confirmed to contain 93% of a 3-hydroxy-5-(phenylsulfanyl) valeric acid unit and other units comprising saturated or unsaturated 3-hydroxyalkanoic acids having 4 to 12 carbon atoms.

Example 26

200 mL of M9 medium containing 0.5% (w/v) of polypeptone were prepared, placed in a 500 mL shake flask, and then sterilized by an autoclave. After the flask was returned to room temperature, a *Pseudomonas cichorii* YN2 strain was inoculated into the medium, which was then cultured with shaking at 30° C. at 125 strokes/min. When a turbidity of the culture medium at 600 nm was 0.1, 0.05% (v/v) of dicyclopropylketone was added to the medium and well stirred. After being cultured with shaking for 14 hours, cells were recovered by centrifugation.

Next, 200 mL of M9 medium containing 0.5% (w/v) of glucose and not containing NH₄Cl as a nitrogen source were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 am, and concentrated with a rotary evaporator, and then the concentrated solution was re-precipitated in cold methanol. Furthermore, only a precipitate was recovered and then vacuum-dried to obtain 160 mg of PHA.

The molecular weight of the thus-obtained PHA was measured by GPC analysis performed by the same method as in Example 1. As a result, Mn=139000 and Mw=309000. As a result of 1H-NMR analysis of the PHA performed by the same method as in Example 1, the PHA was confirmed to contain 86% of a -hydroxy-5-(phenylsulfanyl) valeric acid unit and other units comprising saturated or unsaturated 3-hydroxyalkanoic acids having 4 to 12 carbon atoms.

Example 27

200 mL of M9 medium containing 0.5% (w/v) of polypeptone were prepared, placed in a 500 mL shake flask, and then sterilized by an autoclave. After the flask was returned to room temperature, a *Pseudomonas cichorii* YN2 strain was inoculated into the medium, which was then cultured with shaking at 30° C. at 125 strokes/min. When a turbidity of the culture medium at 600 nm was 0.1, 0.05% (v/v) of dicyclopropylketone was added to the medium and well stirred. After being cultured with shaling for 14 hours, cells were recovered by centrifugation.

Next, 200 mL of M9 medium containing 0.5% (w/v) of glucose was prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, the recovered cells were again suspended in the medium, which was then cultured with at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, concentrated with a rotary evaporator, and then the concentrated solution was re-precipitated in cold methanol. Furthermore, only a precipitate was recovered and then vacuum-dried to obtain 121 mg of PHA.

The molecular weight of the thus-obtained PHA was measured by GPC analysis performed by the same method as in Example 1. As a result, Mn=141000 and Mw=302000. As a result of 1H-NMR analysis of the PHA performed by the same method as in Example 1, the PHA was confirmed to contain 85% of a 3-hydroxy-5-(phenylsulfanyl) valeric acid unit and other units comprising saturated or unsaturated 3-hydroxyalkanoic acids having 4 to 12 carbon atoms.

Example 28

200 mL of M9 medium containing 0.5% (w/v) of polypeptone were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, a *Pseudomonas cichorii* YN2 strain was inoculated into the medium, which was then cultured with shaking at 30° C. at 125 strokes/min. After the shaking culture was continued for 48 hours, cells were recovered by centrifugation.

Next, 200 mL of M9 medium containing 0.5% (w/v) of sodium pyruvate and not containing NH$_4$Cl as a nitrogen source were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, the recovered cells were again suspended in the medium, which was then cultured with shaking at 30° C. at 125 strokes/min. 48 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, and concentrated with a rotary evaporator, and then the concentrated solution was re-precipitated in cold methanol. Furthermore, only a precipitate was recovered, and then vacuum-dried to obtain 145 mg of PHA.

The molecular weight of the thus-obtained PHA was measured by GPC analysis performed by the same method as in Example 1. As a result, Mn=135000 and Mw=288000. As a result of 1H-NMR analysis of the PHA performed by the same method as in Example 1, the PHA was confirmed to contain 72% of a 3-hydroxy-5-(phenylsulfanyl) valeric acid unit, and other units comprising saturated or unsaturated 3-hydroxyalkanoic acids having 4 to 12 carbon atoms.

Example 29

200 mL of M9 medium containing 0.5% (w/v) of polypeptone were prepared, placed in a 500 mL shake flask, and then sterilized by an autoclave. After the flask was returned to room temperature, 0.1% (v/v) of 1-(phenylsulfanyl) pentane sterilized with a filter was added to the medium, and well stirred. Then, a *Pseudomonas cichorii* YN2 strain was inoculated into the medium, which was then cultured with shaking at 30° C. at 125 strokes/min. When a turbidity of the culture medium at 600 nm was 0.1, 0.05% (v/v) of dicyclopropylketone was further added to the medium and well stirred. After the shaking culture was continued for 14 hours, cells were recovered by centrifugation.

Next, 200 mL of M9 medium containing 0.5% (w/v) of sodium pyruvate and not containing NH$_4$Cl as a nitrogen source were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, the recovered cells were again suspended in the medium, which was then cultured with shaking at 30° C. at 125 strokes/min. 48 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, concentrated with a rotary evaporator, and then the concentrated solution was re-precipitated in cold methanol. Furthermore, only a precipitate was recovered and then vacuum-dried to obtain 80 mg of PHA.

The molecular weight of the thus-obtained PHA was measured by GPC analysis performed by the same method as in Example 1. As a result, Mn=129000 and Mw=288000. As a result of 1H-NMR analysis of the PHA performed by the same method as in Example 1, the PHA was confirmed to contain 81% of a 3-hydroxy-5-(phenylsulfanyl) valeric acid unit and other units comprising saturated or unsaturated 3-hydroxyalkanoic acids having 4 to 12 carbon atoms.

Example 30

200 mL of M9 medium containing 0.5% (w/v) of polypeptone were prepared, placed in a 500 mL shake flask, and then sterilized by an autoclave. After the flask was returned to room temperature, a *Pseudomonas cichorii* YN2 strain was inoculated into the medium, which was then cultured with shaking at 30° C. at 125 strokes/min. When a turbidity of the culture medium at 600 nm was 0.1, 0.05% (v/v) of dicyclopropylketone was added to the medium and well stirred. After the shaking culture was continued for 14 hours, cells were recovered by centrifugation.

Next, 200 mL of M9 medium containing 0.5% (w/v) of sodium pyruvate and not containing NH$_4$Cl as a nitrogen source were prepared, placed in a 500 mL shake flask, and then sterilized by an autoclave. After the flask was returned to room temperature, 0.1% (v/v) of 1-(phenylsulfanyl) pentane sterilized with a filter and 0.05% (v/v) of dicyclopropylketone were added to the medium and well stirred. Then, the recovered cells were again suspended in the medium, which was then cultured with shaking at 30° C. at 125 strokes/min. 48 hours thereafter, the cells were recovered by centrifugation, washed once with cold methanol, and then freeze-dried.

The freeze-dried pellets were suspended in 20 mL of chloroform, and stirred at 60° C. for 20 hours to extract the PHA. The resultant extract was filtered through a membrane filter with a pore size of 0.45 μm, and concentrated with a rotary evaporator, and then the concentrated solution was re-precipitated in cold methanol. Furthermore, only a precipitate was recovered and then vacuum-dried to obtain 80 mg of PHA.

The molecular weight of the thus-obtained PHA was measured by GPC analysis performed by the same method as in Example 1. As a result, Mn=131000 and Mw=289000. As a result of 1H-NMR analysis of the PHA performed by the same method as in Example 1, the PHA was confirmed to contain 80% of a 3-hydroxy-5-(phenylsulfanyl) valeric acid unit and other units comprising saturated or unsaturated 3-hydroxyalkanoic acids having 4 to 12 carbon atoms.

Example 31

200 mL of M9 medium containing 0.5% (w/v) of polypeptone were prepared, placed in a 500 mL shake flask, and then sterilized by an autoclave. After the flask was returned to room temperature, a *Pseudomonas cichorii* YN2 strain was inoculated into the medium, which was then cultured with shaking at 30° C. at 125 strokes/min. When a turbidity of the culture medium at 600 nm was 0.1, 0.05% (v/v) of dicyclopropylketone was added to the medium and well stirred. After the shaking culture was continued for 14 hours, cells were recovered by centrifugation.

Next, 200 mL of M9 medium containing 0.5% (w/v) of sodium pyruvate and not containing NH$_4$Cl as a nitrogen source were prepared, placed in a 500 mL shake flask, and then sterilized by an autoclave. After the flask was returned to room temperature, 0.1% (v/v) of 1-(phenylsulfanyl) pentane sterilized with a filter and 0.05% (v/v) of dicyclopropylketone were added to the medium and well stirred. Then, the recovered cells were again suspended in the medium, which was then cultured with shaking at 30° C. at 125 strokes/min. 48 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 µm, and concentrated with a rotary evaporator, and then the concentrated solution was re-precipitated in cold methanol. Furthermore, only a precipitate was recovered and then vacuum-dried to obtain 75 mg of PHA.

The molecular weight of the thus-obtained PHA was measured by GPC analysis performed by the same method as in Example 1. As a result, Mn=131000 and Mw=292000. As a result of 1H-NMR analysis of the PHA performed by the same method as in Example 1, the PHA was confirmed to contain 78% of a 3-hydroxy-5-(phenylsulfanyl) valeric acid unit and other units comprising saturated or unsaturated 3-hydroxyalkanoic acids having 4 to 12 carbon atoms.

Example 32

Colonies of YN2 strain on a M9 agar medium containing 0.1% (w/v) of nonanoic acid were suspended in sterilized physiological saline, and the turbidity at 600 nm was controlled to 1.0. The resultant suspension was coated on 40 plates of M9 agar medium, which did not contain a carbon source, and which was previously prepared, and standing culture was performed at 30° C. in a nonane atmosphere. After standing culture was continued for 48 hours, cells were recovered, and then suspended in 2 ml of physiological saline.

Next, 200 mL of M9 medium containing 0.5% (w/v) of glucose and not containing $NH_4Cl$ as a nitrogen source were prepared, placed in a 500 mL shake flask, and then sterilized by an autoclave. After the flask was returned to room temperature, 0.1% (v/v) of 1-(phenylsulfanyl) pentane sterilized with a filter was added to the medium, and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 µm, and concentrated with a rotary evaporator, and then the concentrated solution was re-precipitated in cold methanol. Furthermore, only a precipitate was recovered and then vacuum-dried to obtain 10 mg of PHA.

The molecular weight of the thus-obtained PHA was measured by GPC analysis performed by the same method as in Example 1. As a result, Mn=128000 and Mw=282000. As a result of 1H-NMR analysis of the PHA performed by the same method as in Example 1, the PHA was confirmed to contain 46% of a 3-hydroxy-5-(phenylsulfanyl) valeric acid unit and other units comprising saturated or unsaturated 3-hydroxyalkanoic acids having 4 to 12 carbon atoms.

Example 33

Colonies of YN2 strain on a M9 agar medium containing 0.1% (w/v) of nonanoic acid were suspended in sterilized physiological saline, and the turbidity at 600 nm was controlled to 1.0. The resultant suspension was coated on 40 plates of M9 agar medium, which did not contain a carbon source and which was previously prepared, and was cultures while standing at 30° C. in a nonane atmosphere. After culturing for 48 hours, cells were recovered and then suspended in 2 ml of a physiological saline.

Next, 200 mL of M9 medium containing 0.5% (w/v) of glucose were prepared, placed in a 500 mL shake flask, and then sterilized by an autoclave. After the flask was returned to room temperature, 0.1% (v/v) of 1-(phenylsulfanyl) pentane sterilized with a filter was added to the medium and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 µm, and concentrated with a rotary evaporator, and then the concentrated solution was re-precipitated in cold methanol. Furthermore, only a precipitate was recovered and then vacuum-dried to obtain 81 mg of PHA.

The molecular weight of the thus-obtained PHA was measured by GPC analysis performed by the same method as in Example 1. As a result, Mn=131000 and Mw=301000. As a result of 1H-NMR analysis of the PHA performed by the same method as in Example 1, the PHA was confirmed to contain 15% of a 3-hydroxy-5-(phenylsulfanyl) valeric acid unit and other units comprising saturated or unsaturated 3-hydroxyalkanoic acids having 4 to 12 carbon atoms.

Example 34

200 mL of M9 medium containing 0.5% (w/v) of glucose were prepared, placed in a 500 mL shake flask, and then sterilized by an autoclave. After the flask was returned to room temperature, 0.1% (v/v) of 1-[(4-methylphenyl)sulfanyl] pentane sterilized with a filter was added to the medium, and well stirred. Then, a *Pseudomonas cichorii* YN2 strain was inoculated into the medium, which was then cultured with shaking at 30° C. at 125 strokes/min. After the shaking culture was continued for 90 hours, cells were recovered by centrifugation.

Next, 200 mL of M9 medium containing 0.5% (w/v) of glucose and not containing $NH_4Cl$ as a nitrogen source were prepared, placed in a 500 mL shake flask, and then sterilized by an autoclave. After the flask was returned to room temperature, 0.1% (v/v) of 1-[(4-methylphenyl)sulfanyl] pentane sterilized with a filter was added to the medium and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 µm, and concentrated with a rotary evaporator, and then the concentrated solution was re-precipitated in cold methanol. Furthermore, only a precipitate was recovered and then vacuum-dried to obtain 74 mg of PHA.

The molecular weight of the thus-obtained PHA was measured by GPC analysis performed by the same method as in Example 1. As a result, Mn=72800 and Mw=143000. As a result of 1H-NMR analysis of the PHA performed by the same method as in Example 1, the PHA was confirmed to contain 40% of a 3-hydroxy-5-[(4-methylphenyl)sulfanyl] valeric acid unit and other units comprising saturated or unsaturated 3-hydroxyalkanoic acids having 4 to 12 carbon atoms.

Example 35

200 mL of M9 medium containing 0.5% (w/v) of glucose were prepared, placed in a 500 mL shake flask, and then sterilized by an autoclave. After the flask was returned to room temperature, 0.1% (v/v) of 1-(phenylsulfanyl) heptane sterilized with a filter was added to the medium and well stirred. Then, a *Pseudomonas cichorii* YN2 strain was inoculated into the medium, which was then cultured with shaking at 30° C. at 125 strokes/min. After being cultured with shaking for 48 hours, cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, and concentrated with a rotary evaporator, and then the concentrated solution was re-precipitated in cold methanol. Furthermore, only a precipitate was recovered and then vacuum-dried to obtain 84 mg of PHA.

The molecular weight of the thus-obtained PHA was measured by GPC analysis performed by the same method as in Example 1. As a result, $Mn=128000$ and $Mw=294000$. As a result of 1H-NMR analysis of the PHA performed by the same method as in Example 1, the PHA was confirmed to contain 40% of a 3-hydroxy-5-(phenylsulfanyl) valeric acid unit, 17% of a 3-hydroxy-7-(phenylsulfanyl) heptanoic acid unit and other units comprising saturated or unsaturated 3-hydroxyalkanoic acids having 4 to 12 carbon atoms.

Example 36

200 mL of M9 medium containing 0.5% (w/v) of glucose were prepared, placed in a 500 mL shake flask, and then sterilized by an autoclave. After the flask was returned to room temperature, 0.1% (v/v) of 1-[(4-fluorophenyl)sulfanyl] pentane sterilized with a filter was added to the medium, and well stirred. Then, a *Pseudomonas cichorii* YN2 strain was inoculated into the medium, which was then cultured with shaking at 30° C. at 125 strokes/min. After being cultued with shaking for 48 hours, cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, and concentrated with a rotary evaporator, and then the concentrated solution was re-precipitated in cold methanol. Furthermore, only a precipitate was recovered and then vacuum-dried to obtain 80 mg of PHA.

The molecular weight of the thus-obtained PHA was measured by GPC analysis performed by the same method as in Example 1. As a result, $Mn=118000$ and $Mw=252000$. As a result of 1H-NMR analysis of the PHA performed by the same method as in Example 1, the PHA was confirmed to contain 76% of a 3-hydroxy-5-[(4-fluorophenyl)sulfanyl] valeric acid unit and other units comprising saturated or unsaturated 3-hydroxyalkanoic acids having 4 to 12 carbon atoms.

Example 37

200 mL of M9 medium containing 0.5% (w/v) of polypeptone were prepared, placed in a 500 mL shake flask, and then sterilized by an autoclave. After the flask was returned to room temperature, 0.1% (v/v) of 1-[(4-cyanophenyl)sulfanyl] pentane sterilized with a filter was added to the medium and well stirred. Then, a *Pseudomonas cichorii* YN2 strain was inoculated into the medium, which was cultured with shaking at 30° C. at 125 strokes/min. After being cultured with shaking for 48 hours, cells were recovered by centrifugation.

Next, 200 mL of M9 medium containing 0.5% (w/v) of glucose were prepared, placed in a 500 mL shake flask, and then sterilized by an autoclave. After the flask was returned to room temperature, 0.1% (v/v) of 1-[(4-cyanophenyl) sulfanyl] pentane sterilized with a filter was added to the medium, and well stirred. Then, the recovered cells were again suspended in the medium, and the shaking culture was performed at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, and concentrated with a rotary evaporator, and then the concentrated solution was re-precipitated in cold methanol. Furthermore, only a precipitate was recovered and then vacuum-dried to obtain 45 mg of PHA.

The molecular weight of the thus-obtained PHA was measured by GPC analysis performed by the same method as in Example 1. As a result, $Mn=68000$ and $Mw=137000$. As a result of 1H-NMR analysis of the PHA performed by the same method as in Example 1, the PHA was confirmed to contain 12% of a 3-hydroxy-5-[(4-cyanophenyl)sulfanyl] valeric acid unit and other units comprising saturated or unsaturated 3-hydroxyalkanoic acids having 4 to 12 carbon atoms.

Example 38

200 mL of M9 medium containing 0.5% (w/v) of glucose were prepared, placed in a 500 mL shake flask, and then sterilized by an autoclave. After the flask was returned to room temperature, 0.1% (v/v) of 1-[(4-nitrophenyl)sulfanyl] pentane sterilized with a filter was added to the medium and well stirred. Then, a *Pseudomonas cichorii* YN2 strain was inoculated into the medium, which was then cultured with shaking at 30° C. at 125 strokes/min. After the shaking culture was continued for 90 hours, cells were recovered by centrifugation.

Next, 200 mL of M9 medium containing 0.5% (w/v) of glucose were prepared, placed in a 500 mL shake flask, and then sterilized by an autoclave. After the flask was returned to room temperature, 0.1% (v/v) of 1-[(4-nitrophenyl)sulfanyl] pentane sterilized with a filter was added to the medium and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, and concentrated with a rotary evaporator, and then the concentrated solution was re-precipitated in cold methanol. Furthermore, only a precipitate was recovered and then vacuum-dried to obtain 20 mg of PHA.

The molecular weight of the thus-obtained PHA was measured by GPC analysis performed by the same method as in Example 1. As a result, Mn=68000 and Mw=137000. As a result of 1H-NMR analysis of the PHA performed by the same method as in Example 1, the PHA was confirmed to contain 5% of a 3-hydroxy-5-[(4-nitrophenyl)sulfanyl] valeric acid unit and other units comprising saturated or unsaturated 3-hydroxyalkanoic acids having 4 to 12 carbon atoms.

Example 39

200 mL of M9 medium containing 0.5% (w/v) of polypeptone were prepared, placed in a 500 mL shake flask, and then sterilized by an autoclave. After the flask was returned to room temperature, 0.1% (v/v) of 1-[(phenylmethyl)sulfanyl] pentane sterilized with a filter was added to the medium, and well stirred. Then, a *Pseudomonas cichorii* YN2 strain was inoculated into the medium, which was then cultured with shaking at 30° C. at 125 strokes/min. After culturing for 48 hours, cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, and concentrated with a rotary evaporator, and then the concentrated solution was re-precipitated in cold methanol. Furthermore, only a precipitate was recovered and then vacuum-dried to obtain 61 mg of PHA.

The molecular weight of the thus-obtained PHA was measured by GPC analysis performed by the same method as in Example 1. As a result, Mn=38000 and Mw=75000. As a result of 1H-NMR analysis of the PHA performed by the same method as in Example 1, the PHA was confirmed to contain 72% of a 3-hydroxy-5-[(phenylmethyl)sulfanyl] valeric acid unit and other units comprising saturated or unsaturated 3-hydroxyalkanoic acids having 4 to 12 carbon atoms.

Example 40

200 mL of M9 medium containing 0.5% (w/v) of glucose were prepared, placed in a 500 mL shake flask, and then sterilized by an autoclave. After the flask was returned to room temperature, 0.1% (v/v) of 1-[(phenylmethyl)sulfanyl] pentane sterilized with a filter was added to the medium, and well stirred. Then, a *Pseudomonas cichorii* YN2 strain was inoculated into the medium, which was then cultured with shaking at 30° C. at 125 strokes/min. After culturing for 48 hours, cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, and concentrated with a rotary evaporator, and then the concentrated solution was re-precipitated in cold methanol. Furthermore, only a precipitate was recovered and then vacuum-dried to obtain 58 mg of PHA.

The molecular weight of the thus-obtained PHA was measured by GPC analysis performed by the same method as in Example 1. As a result, Mn=29000 and Mw=57000. As a result of 1H-NMR analysis of the PHA performed by the same method as in Example 1, the PHA was confirmed to contain 81% of a 3-hydroxy-5-[(phenylmethyl)sulfanyl] valeric acid unit and other units comprising saturated or unsaturated 3-hydroxyalkanoic acids having 4 to 12 carbon atoms.

Example 41

200 mL of M9 medium containing 0.5% (w/v) of glucose were prepared, placed in a 500 mL shake flask, and then sterilized by an autoclave. After the flask was returned to room temperature, 0.1% (v/v) of 1-{[(4-fluorophenyl)methyl]sulfanyl} pentane sterilized with a filter was added to the medium and well stirred. Then, a *Pseudomonas cichorii* YN2 strain was inoculated into the medium, which was then cultured with at 30° C. at 125 strokes/min. After culturing for 48 hours, cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 am, and concentrated with a rotary evaporator, and then the concentrated solution was re-precipitated in cold methanol. Furthermore, only a precipitate was recovered and then vacuum-dried to obtain 80 mg of PHA.

The molecular weight of the thus-obtained PHA was measured by GPC analysis performed by the same method as in Example 1. As a result, Mn=28000 and Mw=55000. As a result of 1H-NMR analysis of the PHA performed by the same method as in Example 1, the PHA was confirmed to contain 73% of a 3-hydroxy-5-{[(4-fluorophenyl)methyl] sulfanyl} valeric acid unit, and other units comprising saturated or unsaturated 3-hydroxyalkanoic acids having 4 to 12 carbon atoms.

Example 42

200 mL of M9 medium containing 0.5% (w/v) of polypeptone were prepared, placed in a 500 mL shake flask, and then sterilized by an autoclave. After the flask was returned to room temperature, 0.1% (v/v) of 1-{[(4-cyanophenyl)methyl]sulfanyl} pentane sterilized with a filter was added to the medium, and well stirred. Then, a *Pseudomonas cichorii* YN2 strain was inoculated into the medium, which was then cultured with at 30° C. at 125 strokes/min. After the shaking culture was continued for 48 hours, cells were recovered by centrifugation.

Next, 200 mL of M9 medium containing 0.5% (w/v) of glucose were prepared, placed in a 500 mL shake flask, and then sterilized by an autoclave. After the flask was returned to room temperature, 0.1% (v/v) of 1-{[(4-cyanophenyl)methyl]sulfanyl} pentane sterilized with a filter was added to the medium, and well stirred. Then, the recovered cells were again suspended in the medium, which was then cultured with shaking at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, and concentrated with a rotary evaporator, and then the concentrated solution was re-precipitated in cold methanol. Furthermore, only a precipitate was recovered and then vacuum-dried to obtain 26 mg of PHA.

The molecular weight of the thus-obtained PHA was measured by GPC analysis performed by the same method as in Example 1. As a result, Mn=32000 and Mw=66000. As a result of 1H-NMR analysis of the PHA performed by the same method as in Example 1, the PHA was confirmed to contain 12% of a 3-hydroxy-5-{[(4-cyanophenyl)methyl]sulfanyl} valeric acid unit and other units comprising saturated or unsaturated 3-hydroxyalkanoic acids having 4 to 12 carbon atoms.

Example 43

200 mL of M9 medium containing 0.5% (w/v) of glucose were prepared, placed in a 500 mL shake flask, and then sterilized by an autoclave. After the flask was returned to room temperature, 0.1% (v/v) of 1-{[(4-nitrophenyl)methyl]sulfanyl} pentane sterilized with a filter was added to the medium and well stirred. Then, a *Pseudomonas cichorii* YN2 strain was inoculated into the medium, which was then cultured with shaking at 30° C. at 125 strokes/min. After culutring for 90 hours, cells were recovered by centrifugation.

Next, 200 mL of M9 medium containing 0.5% (w/v) of glucose were prepared, placed in a 500 mL shake flask, and then sterilized by an autoclave. After the flask was returned to room temperature, 0.1% (v/v) of 1-{[(4-nitrophenyl)methyl]sulfanyl} pentane sterilized with a filter was added to the medium and well stirred. Then, the recovered cells were again suspended in the medium, and the shaking culture was performed at 30° C. at 125 strokes/min. 90 hours thereafter, the cells were recovered by centrifugation, washed once with cold methanol, and then freeze-dried.

The freeze-dried pellets were suspended in 20 mL of chloroform and stirred at 60° C. for 20 hours to extract the PHA. The resultant extract was filtered through a membrane filter with a pore size of 0.45 μm, and concentrated with a rotary evaporator, and then the concentrated solution was re-precipitated in cold methanol. Furthermore, only a precipitate was recovered and then vacuum-dried to obtain 10 mg of PHA.

The molecular weight of the thus-obtained PHA was measured by GPC analysis performed by the same method as in Example 1. As a result, Mn=26000 and Mw=53000. As a result of 1H-NMR analysis of the PHA performed by the same method as in Example 1, the PHA was confirmed to contain 5% of a 3-hydroxy-5-{[(4-nitrophenyl)methyl]sulfanyl} valeric acid unit, and other units comprising saturated or unsaturated 3-hydroxyalkanoic acids having 4 to 12 carbon atoms.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A method of producing polyhydroxyalkanoate by using microorganisms, the method comprising culturing microorganisms capable of producing polyhydroxyalkanoate in a medium containing at least one starting compound selected from the group consisting of substituted alkanes represented by formula (1) to produce polyhydroxyalkanoate having in its molecule at least one unit selected from the group consisting of 3-hydroxy-substituted alkanoate units represented by formula (2):

(1)

wherein R represents a residue containing a substituted aromatic ring, and n represents any integer of 1 to 8;

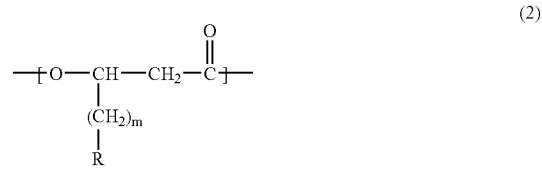

wherein R represents a residue containing a substituted aromatic ring, and n represents any integer of 1 to 8;

wherein in formulas (1) and (2), a residue R containing a substituted aromatic ring is at least one selected from the group consisting of substituted phenylsulfanyl residues represented by formula (3):

wherein R1 represents a substituent of an aromatic ring, and is selected from a H atom, a halogen atom, a CN group, a $NO_2$ group, a $CH_3$ group, a $C_2H_5$ group, a $CH_3CH_2CH_2$ group, a $(CH_3)_2CH$ group, and a $(CH_3)_3C$ group, and the group consisting of (substituted-phenylmethyl)sulfanyl residues represented by formula (4):

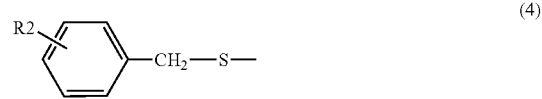

wherein R2 represents a substituent of an aromatic ring, and is selected from a H atom, a halogen atom, a CN group, a $NO_2$ group, a $CH_3$ group, a $C_2H_5$ group, a $CH_3CH_2CH_2$ group, a $(CH_3)_2CH$ group, and a $(CH_3)_3C$ group.

2. A method according to claim 1, wherein n in formula (1) and m in formula (2) have the following relationship (1):

$$m = n - 2 1 \tag{1}$$

wherein 1 represents any integer of $0 \leq 1 < (1/2)n$.

3. A method according to claim 1, wherein the polyhydroxyalkanoate has, in its polymer molecule, a unit represented by formula (2), and at least one of a 3-hydroxyalkanoic acid unit represented by formula (5) and a 3-hydroxy-alka-5-ene acid unit represented by formula (6):

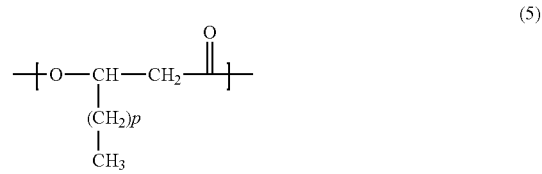

wherein p represents any integer of 0 to 8, and p may be one or more values;

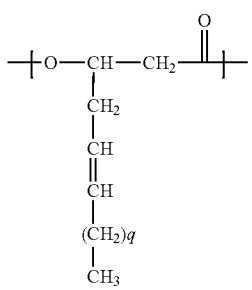
(6)

wherein q represents any integer of 3 to 5, and q may be one or more values.

4. A method according to claim 1, wherein the number average molecular weight of the polyhydroxyalkanoate is in the range of 5000 to 1000000.

5. A method according to claim 1, further comprising a step of culturing the microorganisms in a culture medium containing dicyclopropylketone.

6. A method according to claim 1, wherein the culture medium contains polypeptone.

7. A method according to claim 1, wherein the culture medium contains a yeast extract.

8. A method according to claim 1, wherein the culture medium contains a saccharide.

9. A method according to claim 8, wherein the saccharide is at least one compound selected from the group consisting of glyceroaldehyde, erythrose, arabinose, xylose, glucose, galactose, mannose, fructose, glycerol, erythritol, xylitol, gluconic acid, glucuronic acid, galacturonic acid, maltose, sucrose, and lactose.

10. A method according to claim 1, wherein the culture medium contains an organic acid or its salt.

11. A method according to claim 10, wherein the organic acid or its salt contained in the culture medium is at least one compound selected from the group consisting of pyruvic acid, malic acid, lactic acid, citric acid, succinic acid, and salts thereof.

12. A method according to claim 1, wherein the culture medium contains an amino acid or its salt.

13. A method according to claim 12, wherein the amino acid or its salt contained in the culture medium is at least one compound selected from the group consisting of glutamic acid, asparaginic acid, and salts thereof.

14. A method according to claim 1, wherein the culture medium contains a straight alkanoic acid having 4 to 12 carbon atoms or its salt.

15. A method according to claim 1, wherein the culture step of culturing the microorganisms comprises the two steps of:
   (1) culturing the microorganisms in a culture medium containing at least one substituted alkane selected from the group consisting of substituted alkanes represented by formula (1), and polypeptone; and
   (2) further culturing the microorganisms, which were cultured in step (1), in a culture medium containing at least one substituted alkane selected from the group consisting of substituted alkanes represented by formula (1), and an organic acid or its salt.

16. A method according to claim 1, wherein the culture step of culturing the microorganisms comprises the two steps of:
   (3) culturing the microorganisms in a culture medium containing at least one substituted alkane selected from the group consisting of substituted alkanes represented by formula (1), and a saccharide; and
   (4) further culturing the microorganisms, which were cultured in step (3), in a culture medium containing at least one substituted alkane selected from the group consisting of substituted alkanes represented by formula (1), and a saccharide.

17. A method according to claim 1, wherein the culture step of culturing the microorganisms comprises the two steps of:
   (5) culturing the microorganisms in a culture medium containing at least one substituted alkane selected from the group consisting of substituted alkanes represented by formula (1), and polypeptone; and
   (6) further culturing the microorganisms, which were cultured in step (5), in a culture medium containing at least one substituted alkane selected from the group consisting of substituted alkanes represented by formula (1), and a saccharide.

18. A method according to claim 15, further comprising a step of culturing the microorganisms in a medium containing dicyclopropylketone.

19. A method according to claim 1, wherein the microorganisms have alkane monooxygenase.

20. A method according to claim 19, wherein the microorganisms are *Pseudomonas cichorii* YN2; FERM BP-7375.

* * * * *

UNITED STATES PATENT AND TRADEMARK OFFICE
CERTIFICATE OF CORRECTION

PATENT NO. : 7,056,708 B2
APPLICATION NO. : 10/410349
DATED : June 6, 2006
INVENTOR(S) : Takashi Kenmoku et al.

It is certified that error appears in the above-identified patent and that said Letters Patent is hereby corrected as shown below:

ON TITLE PAGE AT (56) OTHER PUBLICATIONS

Pg. 2 Col. 2 lines 45-47 "Young B. Kim t al., "Poly(β-hydroxyalkanoate) Copolymers Containing Brominated Repeating Units Produced by *Ps udomonas oleovorans*," 25 *Macromol.* 1852-1857 (1992)." should read --Young B. Kim et al., "Poly(β-hydroxyalkanoate) Copolymers Containing Brominated Repeating Units Produced by *Pseudomonas oleovorans*," 25 *Macromol.* 1852-1857 (1992).--;

Pg 2 Col 1 line 21 After "Katharina Fritzsche:", "Polyster" should read --Polyester--;

Pg 2 Col 1 line 29 After "Joanne M. Curley":, "*oleovarans*,"" should read --*oleovorans*,"--;

Pg 2 Col 1 line 52 After "Marianela Andújar et al.," (first occurrence): "*Pseudomonal*" should read --*Pseudomonas*--;

Pg 2 Col. 1 lines 48-50 The second occurrence of "Marianela Andújar et al., "Polyesters Produced by *Pseudomonal oleovorans* Containing Cyclohexyl Groups," 30 *Macromol.* 1611-1615 (1997)" should be deleted;

Col. 1 line 65 After "Roland G. Lageveen": "*oleoverans*" should read --*oleovorans*--;

Col. 2 line 10 After "Alan Grund": "*Pspeudomonas*" should read --*Pseudomonas*--;

Col. 2 line 14 After "Katsutoshi Hori": "*Pseudomonal*" should read --*Pseudomonas*--;

Col.1 line 48 After "Richard A. Gross": "Microbal" should read --Microbial--;

Pg 2 Col. 1 line 35 After "Helmut Ritter": "Chain," should read --Chains,--;

Pg 2 Col 2, line 24 After "Richard Ashby": "Microbal" should read --Microbial--; and Pg 2 Col 2, line 57 After "Moon Yeun Lee": "Microbal" should read --Microbiol--.

COLUMN 1

Line 28, "doe" should read --do--; and
    Line 37, "propertie." should read --properties.--.

UNITED STATES PATENT AND TRADEMARK OFFICE
CERTIFICATE OF CORRECTION

PATENT NO. : 7,056,708 B2
APPLICATION NO. : 10/410349
DATED : June 6, 2006
INVENTOR(S) : Takashi Kenmoku et al.

It is certified that error appears in the above-identified patent and that said Letters Patent is hereby corrected as shown below:

COLUMN 3

Line 52, "be" should --been--.

COLUMN 2

Line 21, "weigh" should read --weight--;
    Line 28, "weigh" should read --weight--;
    Line 34, "Makromol." should read --Macromal.--;
    Line 58, "3-hydroxy-4-phenoxy-n-burylic aid" should read
    --3-hydroxy-4-phenoxy-n-butyric acid--; and
    Line 63, "8-phenxyoctanoic" should read --8-phenoxyoctanoic--.

COLUMN 5

Line 8, "above-descried" should read --above-described--.

COLUMN 6

Line 28, "and n" should read --and m--.

COLUMN 8

Line 34, "staring" should read --starting--.

COLUMN 10

Line 8, "was" should read --as--.

COLUMN 11

Line 65, "1-hexdecene" should read --1-hexadecene--.

COLUMN 14

Line 54, "s" should read --as--.

COLUMN 16

Line 27, "perfomred" should read --performed--.

UNITED STATES PATENT AND TRADEMARK OFFICE
CERTIFICATE OF CORRECTION

PATENT NO. : 7,056,708 B2
APPLICATION NO. : 10/410349
DATED : June 6, 2006
INVENTOR(S) : Takashi Kenmoku et al.

It is certified that error appears in the above-identified patent and that said Letters Patent is hereby corrected as shown below:

COLUMN 20

Line 40, "cultuered" should read --cultured--; and
Line 50, "0.1% (v/)" should read --0.1% (v/v)--.

COLUMN 21

Line 4, "-hydroxy" should read --3-hydroxy--.

COLUMN 24

Line 18, "cultuerd" should read --cultured--; and
Line 65, "was added" should read --was--.

COLUMN 27

Line 4, "0.45 am," should read --0.45 µm,--; and
Line 52, "-hydroxy" should read --3-hydroxy--.

COLUMN 30

Line 4, "0.45 am," should read --0.45 µm,--;
Line 14, "-hydroxy" should read --3-hydroxy--; and
Line 27, "shaling" should read --shaking--.

COLUMN 34

Line 1, "cultures" should read --cultured--.

COLUMN 38

Line 19, "0.45 am," should read --0.45 µm,--.

UNITED STATES PATENT AND TRADEMARK OFFICE
CERTIFICATE OF CORRECTION

PATENT NO. : 7,056,708 B2
APPLICATION NO. : 10/410349
DATED : June 6, 2006
INVENTOR(S) : Takashi Kenmoku et al.

It is certified that error appears in the above-identified patent and that said Letters Patent is hereby corrected as shown below:

COLUMN 39

Line 16, "culutring" should read --culturing--.

Signed and Sealed this

Twenty-sixth Day of December, 2006

JON W. DUDAS
*Director of the United States Patent and Trademark Office*